(12) United States Patent
Pesach et al.

(10) Patent No.: US 12,727,966 B2
(45) Date of Patent: Sep. 8, 2026

(54) SYSTEM, DEVICE AND METHODS FOR DENTAL DIGITAL IMPRESSIONS

(71) Applicant: LUMINX IL LTD, Hod HaSharon (IL)

(72) Inventors: Benny Pesach, Rosh Haayin (IL); Georgy Melamed, Ramat Gan (IL); Blanc Zach Lehr, Tel-Aviv (IL); Ygael Grad, Tel-Aviv (IL); Amitai Reuvenny, Kfar-Saba (IL)

(73) Assignee: LUMINX IL LTD

( * ) Notice: Subject to any disclaimer, the term of this patent is extended or adjusted under 35 U.S.C. 154(b) by 508 days.

(21) Appl. No.: 17/527,046

(22) Filed: Nov. 15, 2021

(65) Prior Publication Data

US 2022/0071737 A1 Mar. 10, 2022

Related U.S. Application Data

(63) Continuation of application No. 16/227,995, filed on Dec. 20, 2018, now Pat. No. 11,173,011, which is a (Continued)

(51) Int. Cl.
*A61C 1/08* (2006.01)
*A61B 34/20* (2016.01)
(Continued)

(52) U.S. Cl.
CPC .............. *A61C 1/082* (2013.01); *A61B 34/20* (2016.02); *A61C 1/003* (2013.01); *A61C 1/0069* (2013.01);
(Continued)

(58) Field of Classification Search
CPC ........... A61C 1/082; A61C 5/70; A61C 1/003; A61C 1/0069; A61C 1/08; A61C 3/02; A61C 9/0053; A61C 19/04; A61B 34/20
See application file for complete search history.

(56) References Cited

U.S. PATENT DOCUMENTS 3,634,938 A 1/1972 Hutchinson
4,279,598 A 7/1981 Scheicher
(Continued)

FOREIGN PATENT DOCUMENTS

CN 101677757 A 3/2010
EP 1901033 A1 3/2008
(Continued)

OTHER PUBLICATIONS

Communication Pursuant to Article 94(3) EPC Dated Nov. 16, 2021 From the European Patent Office Re. Application No. 17707964.7. (4 Pages).

(Continued)

*Primary Examiner* — Nicholas D Lucchesi
(74) *Attorney, Agent, or Firm* — FENWICK & WEST LLP

(57) ABSTRACT

Methods and systems for tracking a dental tool within an oral cavity for taking and/or updating of a dental impression are described. In some embodiments, a marker, optionally a magnetic marker, is coupled to position movements of a rotatable dental tool. In some embodiments, detected movements of the marker are used, optionally in combination with other tracking data, to map contours which a portion of the rotatable dental tool follows during interaction with a dental surface. Optionally, the interaction occurs during grinding, drilling, and/or other procedures; which may be preparatory, for example, to the manufacture and/or fitting of a dental prosthetic.

19 Claims, 15 Drawing Sheets

Related U.S. Application Data continuation of application No. 15/571,231, filed as application No. PCT/IL2016/050449 on May 1, 2016, now Pat. No. 10,159,542.

(60) Provisional application No. 62/155,521, filed on May 1, 2015.

(51) Int. Cl.

| | |
|---|---|
| ***A61C 1/00*** | (2006.01) |
| ***A61C 3/02*** | (2006.01) |
| ***A61C 5/70*** | (2017.01) |
| ***A61C 9/00*** | (2006.01) |
| ***A61C 19/04*** | (2006.01) |
| *A61B 90/00* | (2016.01) |
| *A61B 90/30* | (2016.01) |

(52) U.S. Cl.

CPC .................. *A61C 1/08* (2013.01); *A61C 3/02* (2013.01); *A61C 5/70* (2017.02); *A61C 9/0053* (2013.01); *A61C 19/04* (2013.01); *A61B 2034/2048* (2016.02); *A61B 2034/2051* (2016.02); *A61B 2034/2057* (2016.02); *A61B 2034/2065* (2016.02); *A61B 2034/2072* (2016.02); *A61B 2090/064* (2016.02); *A61B 2090/306* (2016.02); *A61B 2090/309* (2016.02); *A61B 2090/3614* (2016.02); *A61B 2090/371* (2016.02); *A61B 2090/3937* (2016.02); *A61B 2090/3958* (2016.02); *A61B 2090/3991* (2016.02)

(56) References Cited

U.S. PATENT DOCUMENTS 4,478,580 A 10/1984 Barrut
4,571,180 A 2/1986 Kulick
4,665,621 A * 5/1987 Ackerman .......... A61C 19/043 33/513
4,764,114 A 8/1988 Jeffcoat et al.
4,790,751 A 12/1988 Reinhardt et al.
4,823,809 A 4/1989 Gott, Jr. et al.
4,873,651 A 10/1989 Raviv
4,883,425 A 11/1989 Zimble
4,935,635 A 6/1990 O'Harra
5,049,070 A 9/1991 Ademovic
5,051,823 A 9/1991 Cooper et al.
5,176,687 A 1/1993 Hasson et al.
5,178,536 A 1/1993 Werly et al.
5,178,537 A 1/1993 Currie
5,190,456 A 3/1993 Hasegawa
5,215,521 A 6/1993 Cochran et al.
5,224,049 A * 6/1993 Mushabac .......... G05B 19/4207 264/222
5,230,621 A 7/1993 Jacoby
5,244,387 A 9/1993 Fuierer
5,257,184 A 10/1993 Mushabac
5,313,053 A 5/1994 Koenck et al.
5,318,442 A 6/1994 Jeffcoat et al.
5,320,462 A * 6/1994 Johansson .......... A61F 2/30942 356/601
5,368,597 A 11/1994 Pagedas
5,372,502 A 12/1994 Massen et al.
5,423,677 A 6/1995 Brattesani
5,435,722 A 7/1995 Mandell
5,618,296 A 4/1997 Sorensen et al.
5,634,790 A 6/1997 Pathmanabhan et al.
5,743,731 A 4/1998 Lares et al.
5,850,289 A 12/1998 Fowler et al.
5,862,559 A 1/1999 Hunter
5,897,509 A 4/1999 Toda et al.
5,919,129 A 7/1999 Vandre
5,944,523 A 8/1999 Badoz
5,969,321 A * 10/1999 Danielson .......... G06K 7/10811 235/462.23
5,993,209 A 11/1999 Matoba et al.
6,000,939 A 12/1999 Ray et al.
6,007,333 A 12/1999 Callan et al.
6,116,899 A 9/2000 Takeuchi
6,142,936 A 11/2000 Beane et al.
6,179,611 B1 1/2001 Everett et al.
6,241,519 B1 6/2001 Sedelmayer
6,257,889 B1 7/2001 Boston
6,276,934 B1 8/2001 Rakocz
6,309,219 B1 10/2001 Robert
6,406,440 B1 6/2002 Stefanchik
6,423,803 B1 7/2002 Nagpal et al.
6,468,079 B1 10/2002 Fischer et al.
6,819,318 B1 11/2004 Geng
6,885,464 B1 4/2005 Pfeiffer et al.
7,041,056 B2 5/2006 Deslauriers et al.
7,056,329 B2 6/2006 Kerr
7,097,648 B1 8/2006 Globerman et al.
7,346,417 B2 3/2008 Lueth et al.
7,494,338 B2 2/2009 Durbin et al.
7,625,335 B2 12/2009 Deichmann et al.
7,668,583 B2 2/2010 Fegert et al.
7,766,823 B2 8/2010 Moll et al.
7,813,591 B2 10/2010 Paley et al.
8,280,152 B2 10/2012 Thiel et al.
8,287,561 B2 10/2012 Nunez et al.
8,371,848 B2 2/2013 Okawa et al.
8,439,682 B1 5/2013 Heath et al.
8,744,194 B2 6/2014 Kawasaki et al.
8,764,646 B2 7/2014 Grundeman
8,936,470 B2 1/2015 Pruckner et al.
9,137,511 B1 9/2015 LeGrand, III et al.
9,179,987 B2 11/2015 Goodacre
9,463,081 B2 10/2016 Urakabe
9,522,054 B2 12/2016 Kim et al.
9,603,675 B2 3/2017 Pruckner
9,918,805 B2 3/2018 Pruckner
10,136,970 B2 11/2018 Pesach
10,182,875 B2 1/2019 Yates et al.
10,206,666 B2 2/2019 Dickson et al.
10,226,599 B2 3/2019 Schaffer
10,299,880 B2 5/2019 Ramirez Luna et al.
10,470,846 B2 11/2019 Kopelman et al.
10,695,150 B2 6/2020 Kopelman et al.
2002/0037490 A1 3/2002 Oyamada et al.
2002/0103420 A1 8/2002 Coleman et al.
2002/0133096 A1 9/2002 Toda et al.
2004/0041996 A1 3/2004 Abe
2004/0087937 A1 5/2004 Eggers et al.
2004/0097792 A1 5/2004 Moll et al.
2004/0106868 A1 6/2004 Liew et al.
2004/0117052 A1 6/2004 Geng
2004/0158261 A1 8/2004 Vu
2004/0191725 A1 9/2004 Szymaitis
2005/0116673 A1 6/2005 Carl et al.
2006/0085005 A1 4/2006 Kenealy, III et al.
2006/0154198 A1 7/2006 Durbin et al.
2007/0037125 A1 2/2007 Maev et al.
2007/0042315 A1 2/2007 Boutoussov et al.
2007/0064242 A1 3/2007 Childers
2007/0065782 A1 3/2007 Maschke
2007/0172112 A1 7/2007 Paley et al.
2007/0225744 A1 9/2007 Nobles et al.
2007/0260231 A1 11/2007 Rose et al.
2008/0002011 A1 1/2008 Mizutani et al.
2008/0002869 A1 1/2008 Scharlack et al.
2008/0038688 A1 2/2008 Kopelman et al.
2008/0145817 A1 6/2008 Brennan et al.
2008/0160477 A1 7/2008 Stookey et al.
2008/0201101 A1 8/2008 Hebert et al.
2008/0234579 A1 9/2008 Halevy-Politch et al.
2008/0255498 A1 10/2008 Houle
2008/0261165 A1 10/2008 Steingart et al.
2009/0017416 A1 1/2009 Nguyen et al.
2009/0043314 A1 2/2009 Sevensson et al.
2009/0061383 A1 3/2009 Kang
2009/0087050 A1 4/2009 Gandyra

(56) References Cited

U.S. PATENT DOCUMENTS

2009/0306506 A1 12/2009 Heger et al.
2009/0326383 A1 12/2009 Barnes et al.
2010/0047733 A1 2/2010 Nahlieli
2010/0092908 A1 4/2010 Rothenwaender et al.
2010/0189341 A1 7/2010 Oota et al.
2010/0238279 A1 9/2010 Thoms et al.
2010/0239136 A1 9/2010 Gandyra et al.
2010/0239996 A1 9/2010 Ertl
2010/0268069 A1 10/2010 Liang
2010/0268071 A1 10/2010 Kim
2010/0303341 A1 12/2010 Häusler
2010/0305435 A1 12/2010 Magill
2011/0184245 A1 7/2011 Xia et al.
2011/0184432 A1 7/2011 Parihar et al.
2011/0190781 A1 8/2011 Collier et al.
2011/0301419 A1 12/2011 Craft et al.
2012/0015329 A1 1/2012 Gross et al.
2012/0040305 A1 2/2012 Karazivan et al.
2012/0046536 A1 2/2012 Cheung et al.
2012/0062557 A1 3/2012 Dillon et al.
2012/0097002 A1 4/2012 Thiedig
2012/0179281 A1 7/2012 Steingart et al.
2012/0189182 A1 7/2012 Liang et al.
2012/0270177 A1 10/2012 Nakashima et al.
2012/0271176 A1 10/2012 Moghaddam et al.
2013/0000666 A1 1/2013 Hu
2013/0017507 A1 1/2013 Moffson et al.
2013/0027515 A1 1/2013 Vinther et al.
2013/0060144 A1 3/2013 Culjat et al.
2013/0188012 A1 7/2013 Bellis et al.
2013/0209953 A1 8/2013 Arlinsky et al.
2013/0236850 A1 9/2013 Wu et al.
2013/0253278 A1 9/2013 Smith
2013/0273492 A1 10/2013 Suttin, Sr. et al.
2014/0066784 A1 3/2014 Yokota
2014/0093835 A1 4/2014 Levin
2014/0111616 A1 4/2014 Blayvas
2014/0120492 A1 5/2014 Loannidis et al.
2014/0120493 A1 5/2014 Levin
2014/0146142 A1 5/2014 Duret et al.
2014/0178832 A1 6/2014 Choi et al.
2014/0194696 A1 7/2014 Fischvogt
2014/0199650 A1* 7/2014 Moffson ................ A61B 5/682 600/409
2014/0212832 A1 7/2014 Fisker et al.
2014/0221819 A1 8/2014 Sarment
2014/0248577 A1 9/2014 Tahmasebi et al.
2014/0276055 A1 9/2014 Barthe et al.
2014/0309523 A1 10/2014 Daon et al.
2014/0330285 A1 11/2014 Rosenblatt et al.
2014/0343395 A1* 11/2014 Choi .................... A61B 5/4851 600/409
2015/0015701 A1 1/2015 Yu
2015/0118638 A1 4/2015 Cowburn
2015/0182299 A1 7/2015 Koubi et al.
2015/0223910 A1 8/2015 Pruckner
2015/0223916 A1 8/2015 Kim et al.
2015/0229911 A1 8/2015 Ge et al.
2015/0297254 A1 10/2015 Sullivan et al.
2015/0348320 A1 12/2015 Pesach et al.
2016/0100857 A1 4/2016 Wachli et al.
2016/0120615 A1 5/2016 Scurtescu
2016/0163115 A1 6/2016 Furst
2016/0259515 A1 9/2016 Sabina et al.
2016/0262856 A1 9/2016 Atiya et al.
2016/0270878 A1 9/2016 Fulton, III
2016/0338682 A1 11/2016 Hoyte et al.
2016/0338803 A1 11/2016 Pesach
2017/0007377 A1 1/2017 Pesach et al.
2017/0128059 A1 5/2017 Coe et al.
2017/0173262 A1 6/2017 Veltz
2017/0202483 A1 7/2017 Sorimoto et al.
2017/0215997 A1 8/2017 Martin
2018/0049830 A1 2/2018 Yates et al.
2018/0318051 A1 11/2018 Lu et al.
2018/0360481 A1 12/2018 Bonadio et al.
2019/0125297 A1 5/2019 Chan et al.
2019/0192262 A1 6/2019 Pesach
2019/0247033 A1 8/2019 Yaari
2019/0262098 A1 8/2019 Pesach et al.
2019/0343598 A1 11/2019 Knobel et al.
2020/0060550 A1 2/2020 Pesach et al.
2020/0155274 A1 5/2020 Pimenov et al.
2020/0155285 A1 5/2020 Pesach et al.
2020/0268410 A1 8/2020 Yaari et al.
2021/0321872 A1 10/2021 Saphier et al.
2022/0151756 A1 5/2022 Pesach et al.
2023/0181295 A1 6/2023 Pesach et al.
2023/0285124 A1 9/2023 Pesach et al.
2024/0058109 A1 2/2024 Pesach et al.

FOREIGN PATENT DOCUMENTS

EP 2165674 A1 3/2010
EP 2630929 B1 8/2013
ES 2115544 A1 6/1998
FR 2692773 A1 12/1993
GB 2495522 A 3/2013
JP 63-005742 A 1/1988
JP 07-155297 A 6/1995
JP 10-165425 A 6/1998
JP H10-262996 A 10/1998
JP 11-192207 A 7/1999
JP 2002-125927 A 5/2002
JP 2003-325451 A 11/2003
JP 2006-102497 A 4/2006
JP 2007-152004 A 6/2007
JP 2007-296249 A 11/2007
JP 2009-268614 A 11/2009
JP 2010-104652 A 5/2010
JP 2012-016573 A 1/2012
JP 5016311 B2 6/2012
JP 2014-236957 A 12/2014
JP 5661255 B2 1/2015
KR 10-1782740 B1 9/2017
WO WO 98/06352 A1 2/1998
WO WO 2004/002327 A1 1/2004
WO WO 2005/104959 A1 11/2005
WO WO 2007/063980 A1 6/2007
WO WO 2008/013181 A1 1/2008
WO WO 2014/020247 A1 2/2014
WO WO 2014/102779 A2 7/2014
WO WO 2015/028646 A1 3/2015
WO WO 2015/107520 A1 7/2015
WO WO 2016/028789 A2 2/2016
WO WO 2016/064617 A1 4/2016
WO WO 2016/110855 A1 7/2016
WO WO 2016/113745 A1 7/2016
WO WO 2016/178212 A1 11/2016
WO WO 2017/125926 A2 7/2017
WO WO 2017/216803 A1 12/2017
WO WO 2018/047180 A1 8/2018
WO WO 2019/008586 A1 1/2019
WO WO 2019/021285 A1 1/2019
WO WO 2019/049152 A1 3/2019
WO WO 2020/144692 A2 7/2020

OTHER PUBLICATIONS

European Search Report and the European Search Opinion Dated Jan. 3, 2022 From the European Patent Office Re. Application No. 21200149.9. (10 Pages).
Invitation to Pay Additional Fees Dated May 12, 2020 From the International Searching Authority Re. Application No. PCT/IL2020/050040. (3 Pages).
Invitation to Pay Additional Fees, Communication Relating to the Results of the Partial International Search and the Provisional Opinion Dated Nov. 17, 2017 From the International Searching Authority Re. Application No. PCT/IL2017/051015. (17 Pages).
Communication Pursuant to Article 94(3) EPC Dated Jul. 1, 2022 From the European Patent Office Re. Application No. 18837606.5. (4 Pages).

(56) References Cited

OTHER PUBLICATIONS

Final Official Action Dated Jun. 15, 2022 from US Patent and Trademark Office Re. U.S. Appl. No. 16/634,152. (19 pages).
Communication Pursuant to Article 94(3) EPC Dated Oct. 4, 2023 From the European Patent Office Re. Application No. 18837606.5, (4 Pages).
Communication Pursuant to Article 94(3) EPC Dated Jul. 21, 2023 From the European Patent Office Re. Application No. 18837606.5, (5 Pages).
Notice of Allowance Dated Jul. 6, 2023 From the US Patent and Trademark Office Re. U.S. Appl. No. 16/628,656, (8 Pages).
Official Action Dated May 10, 2023 from the US Patent and Trademark Office Re. U.S. Appl. No. 17/211,640, (12 pages).
Requisition by the Examiner Dated May 2, 2023 From the Innovation, Science and Economic Development Canada, Canadian Intellectual Property Office Re. Application No. 3,153,949, (4 Pages).
Final Official Action Dated Mar. 6, 2023 from the US Patent and Trademark Office Re: U.S. Appl. No. 16/628,656, 22 pages.
Communication Pursuant to Article 94(3) EPC Dated Nov. 21, 2023 From the European Patent Office Re. Application No. 21200149.9, (5 Pages).
Applicant-Initiated Interview Summary Dated Aug. 2, 2017 From the US Patent and Trademark Office Re. U.S. Appl. No. 15/115,196. (3 pages).
Communication Pursuant to Article 94(3) EPC Dated Oct. 5, 2021 From the European Patent Office Re. Application No. 18759184.7. (6 Pages).
Communication Pursuant to Article 94(3) EPC Dated Oct. 7, 2020 From the European Patent Office Re. Application No. 177805300.6. (5 Pages).
Communication Pursuant to Article 94(3) EPC Dated Aug. 10, 2017 From the European Patent Office Re. Application No. 13830124.7. (6 Pages).
Communication Pursuant to Article 94(3) EPC Dated Nov. 19, 2018 From the European Patent Office Re. Application No. 13830124.7. (8 Pages).
Communication Pursuant to Article 94(3) EPC Dated Nov. 19, 2020 From the European Patent Office Re. Application No. 13830124.7. (6 Pages).
Communication Pursuant to Article 94(3) EPC Dated Jan. 29, 2021 From the European Patent Office Re. Application No. 18769813.9. (9 Pages).
Communication Pursuant to Article 94(3) EPC Dated Nov. 30, 2021 From the European Patent Office Re. Application No. 17780530.6. (4 Pages).
Communication Pursuant to Article 94(3) EPC Dated Jan. 31, 2020 From the European Patent Office Re. Application No. 17780530.6. (3 Pages).
Communication Pursuant to Rules 70(2) and 70a(2) EPC Dated Sep. 7, 2018 From the European Patent Office Re. Application No. 16789407.0. (1 Page).
Communication Relating to the Results of the Partial International Search and the Provisional Opinion Dated Jun. 14, 2017 From the International Searching Authority Re. Application No. PCT/IL2017/050072. (12 Pages).
Communication Relating to the Results of the Partial International Search Dated May 8, 2014 From the International Searching Authority Re. Application No. PCT/IL2013/051059. (7 Pages).
Decision of Rejection Dated Jan. 14, 2020 From the Japan Patent Office Re. Application No. 2017-228103 and Its Translation Into English. (7 Pages).
English Translation of Ground(s) of Reason of Rejection Dated Nov. 19, 2021 From the Korean Intellectual Property Office Re. Application No. 2010-7032325. (2 Pages).
European Search Report and the European Search Opinion Dated Feb. 4, 2020 From the European Patent Office Re. Application 19211372.8. (10 Pages).
Final Official Action Dated Dec. 28, 2020 from the US Patent and Trademark Office Re. U.S. Appl. No. 16/634,152. (29 pages).
Ground(s) of Reason of Rejection Dated Nov. 19, 2021 From the Korean Intellectual Property Office Re. Application No. 2010-7032325. (2 Pages).
International Preliminary Report on Patentability Dated Aug. 2, 2018 From the International Bureau of WIPO Re. Application No. PCT/IL2017/050072. (10 Pages).
International Preliminary Report on Patentability Dated Feb. 6, 2020 From the International Bureau of WIPO Re. Application No. PCT/IL2018/050825. (10 Pages).
International Preliminary Report on Patentability Dated Jul. 9, 2015 From the International Bureau of WIPO Re. Application No. PCT/IL2013/051059. (17 Pages).
International Preliminary Report on Patentability Dated Jan. 16, 2020 From the International Bureau of WIPO Re. Application No. PCT/IL2018/050731. (9 Pages).
International Preliminary Report on Patentability Dated Nov. 16, 2017 From the International Bureau of WIPO Re. Application No. PCT/IL2016/050449. (11 Pages).
International Preliminary Report on Patentability Dated Mar. 19, 2020 From the International Bureau of WIPO Re. Application No. PCT/IL2017/051014. (10 Pages).
International Preliminary Report on Patentability Dated Jul. 20, 2017 From the International Bureau of WIPO Re. Application No. PCT/IL2016/050023. (10 Pages).
International Preliminary Report on Patentability Dated Mar. 21, 2019 From the International Bureau of WIPO Re. Application No. PCT/IL2017/051015. (13 Pages).
International Preliminary Report on Patentability Dated Jul. 22, 2021 From the International Bureau of WIPO Re. Application No. PCT/IL2020/050040. (10 Pages).
International Preliminary Report on Patentability Dated Jul. 27, 2017 From the International Bureau of WIPO Re. Application No. PCT/IL2016/050058. (7 Pages).
International Search Report and the Written Opinion Dated Oct. 1, 2018 From the International Searching Authority Re. Application No. PCT/IL2018/050731. (16Pages).
International Search Report and the Written Opinion Dated Sep. 2, 2014 From the International Searching Authority Re. Application No. PCT/IL2013/051059. (22 Pages).
International Search Report and the Written Opinion Dated Nov. 7, 2018 From the International Searching Authority Re. Application No. PCT/IL2018/050825. (17 Pages).
International Search Report and the Written Opinion Dated Aug. 8, 2017 From the International Searching Authority Re. Application No. PCT/IL2017/050072. (17 Pages).
International Search Report and the Written Opinion Dated Dec. 11, 2018 From the International Searching Authority Re. Application No. PCT/IL2017/051014. (18 Pages).
International Search Report and the Written Opinion Dated Apr. 18, 2016 From the International Searching Authority Re. Application No. PCT/IL2016/050058. (12 Pages).
International Search Report and the Written Opinion Dated Apr. 21, 2016 From the International Searching Authority Re. Application No. PCT/IL2016/050023. (12 Pages).
International Search Report and the Written Opinion Dated Aug. 23, 2016 From the International Searching Authority Re. Application No. PCT/IL2016/050449. (17 Pages).
International Search Report and the Written Opinion Dated Jul. 23, 2020 From the International Searching Authority Re. Application No. PCT/IL2020/050040. (14 Pages).
International Search Report and the Written Opinion Dated Jan. 24, 2018 From the International Searching Authority Re. Application No. PCT/IL2017/051015. (23 Pages).
Notice of Allowance Dated Aug. 9, 2018 From the US Patent and Trademark Office Re. U.S. Appl. No. 15/571,231. (17 pages).
Notice of Allowance Dated Jul. 11, 2018 From the US Patent and Trademark Office Re. U.S. Appl. No. 15/115,196. (8 pages).
Notice of Allowance Dated May 12, 2016 From the US Patent and Trademark Office Re. U.S. Appl. No. 14/655,286. (16 Pages).
Notice of Allowance Dated Jul. 13, 2021 from the US Patent and Trademark Office Re. U.S. Appl. No. 16/227,995. (7 pages).
Notice of Allowance Dated Nov. 30, 2020 from the US Patent and Trademark Office Re. U.S. Appl. No. 16/071,058. (10 pages).

(56) References Cited

OTHER PUBLICATIONS

Notice of Reasons for Rejection Dated May 7, 2019 From the Japan Patent Office Re. Application No. 2017-228103 and Its Translation Into English. (8 Pages).
Notice of Reasons for Rejection Dated Jul. 11, 2017 From the Japan Patent Office Re. Application No. 2015-548888 and Its Translation Into English. (5 Pages).
Notice of Reasons for Rejection Dated Feb. 14, 2017 From the Japan Patent Office Re. Application No. 2015-548888 and Its Translation Into English. (10 Pages).
Notice of Reasons for Rejection Dated Sep. 25, 2018 From the Japan Patent Office Re. Application No. 2017-228103 and Its Translation Into English. (15 Pages).
Notice Requesting Submission of Opinion Dated Feb. 3, 2021 From the Korean Intellectual Property Office Re. Application No. 10-2020-7032325 and Its Translation Into English. (14 Pages).
Notice Requesting Submission of Opinion Dated Jan. 21, 2020 From the Korean Intellectual Property Office Re. Application No. 10-2019-7034814. (3 Pages).
Notice Requesting Submission of Opinion Dated Apr. 26, 2019 From the Korean Intellectual Property Office Re. Application No. 10-2015-7020305. (4 Pages).
Notification of Office Action and Search Report Dated Jan. 5, 2017 From the State Intellectual Property Office of the People's Republic of China Re. Application No. 201380071840.0. (7 Pages).
Notification of Office Action Dated Apr. 15, 2016 From the State IntellectualProperty Office of the People's Republic of China Re. Application No. 201380071840.0. (3 Pages).
Office Action Dated Aug. 6, 2019 From the Israel Patent Office Re. Application No. 264237 and Its Translation Into English. (6 Pages).
Official Action Dated Sep. 3, 2021 from the US Patent and Trademark Office Re. U.S. Appl. No. 16/634,152. (43 pages).
Official Action Dated Nov. 4, 2020 From the US Patent and Trademark Office Re. U.S. Appl. No. 15/274,756. (19 Pages).
Official Action Dated Mar. 9, 2017 From the US Patent and Trademark Office Re. U.S. Appl. No. 15/115,196. (26 pages).
Official Action Dated Jun. 12, 2020 From the US Patent and Trademark Office Re. U.S. Appl. No. 16/634,152. (41 pages).
Official Action Dated Dec. 13, 2017 From the US Patent and Trademark Office Re. U.S. Appl. No. 15/115,196. (26 pages).
Official Action Dated Jun. 13, 2019 From the US Patent and Trademark Office Re. U.S. Appl. No. 15/274,756. (39 pages).
Official Action Dated May 15, 2020 from the US Patent and Trademark Office Re. U.S. Appl. No. 16/071,058. (31 pages).
Official Action Dated Feb. 19, 2021 From the US Patent and Trademark Office Re. U.S. Appl. No. 16/227,995. (27 Pages).
Official Action Dated Sep. 28, 2016 From the US Patent and Trademark Office Re. U.S. Appl. No. 15/115,196. (19 pages).
Official Action Dated Apr. 3, 2020 from the US Patent and Trademark Office Re. U.S. Appl. No. 16/199,954. (31 pages).
Requisition by the Examiner Dated Oct. 4, 2019 From the Innovation, Science and Economic Development Canada, Canadian Intellectual Property Office Re. Application No. 2,896,210. (3 Pages).
Restriction Official Action Dated Nov. 14, 2019 From the US Patent and Trademark Office Re. U.S. Appl. No. 16/199,954. (6 pages).
Restriction Official Action Dated Sep. 26, 2018 From the US Patent and Trademark Office Re. U.S. Appl. No. 15/274,756. (10 Pages).
Summons to Attend Oral Proceedings Pursuant to Rule 115(1) EPC Dated Mar. 19, 2020 From the European Patent Office Re. Application No. 13830124.7. (13 Pages).
Summons to Attend Oral Proceedings Pursuant to Rule 115(1) EPC Dated Mar. 19, 2021 From the European Patent Office Re. Application No. 17780530.6. (7 Pages).
Summons to Attend Oral Proceedings Pursuant to Rule 115(1) EPC Dated Apr. 20, 2021 From the European Patent Office Re. Application No. 17780530.6. (2 Pages).
Supplementary European Search Report and the European Search Opinion Dated Feb. 19, 2021 From the European Patent Office Re. Application No. 18837606.5. (7 Pages).
Supplementary European Search Report and the European Search Opinion Dated Aug. 21, 2018 From the European Patent Office Re. Application No. 16789407.0. (6 Pages).
Translation Dated Feb. 2, 2020 of Notice Requesting Submission of Opinion Dated Jan. 21, 2020 From the Korean Intellectual Property Office Re. Application No. 10-2019-7034814. (3 Pages).
Translation Dated May 9, 2019 of Notice Requesting Submission of Opinion Dated Apr. 26, 2019 From the Korean Intellectual Property Office Re. Application No. 10-2015-7020305. (4 Pages).
Translation Dated Nov. 30, 2021 of Ground(s) of Reason of Rejection Dated Nov. 19, 2021 From the Korean Intellectual Property Office Re. Application No. 2010-7032325. (2 Pages).
Translation of Notification of Apr. 15, 2016 From the State Intellectual Property Office of the People's Republic of China Re. Application No. 201380071840.0. (2 Pages).
Translation of Notification of Office Action Dated Jan. 5, 2017 From the State Intellectual Property Office of the People's Republic of China Re. Application No. 201380071840.0. (4 Pages).
Bouget et al. "3D Photography Using Shadows in Dual-Space Geometry", The International Journal of Computer Vision, 35(2): 129-149, Nov./Dec. 1999.
Fluegge et al. "Precision of Intraoral Digital Dental Impressions With Intraoral and Extraoral Digitization With the iTero and a Model Scanner", American Journal of Orthodontics and Dentofacial Orthopedics, 144(3): 471-478, Sep. 2013.
Geng "Structured-Light 3D Surface Imaging: A Tutorial", Advances in Optics and Photonics, 3: 128-160, 2011.
Goshtasby et al. "A System for Digital Reconstruction of Gypsum Dental Casts", IEEE Transactions on Medical Imaging, 16(5): , Oct. 1997.
Logozzo et al. "Recent Advances in Dental Optics—Part I: 3D Intraoral Scanners for Restorative Dentistry", Optics and Lasers in Engineering, 54: 203-221, Mar. 2014.
Maintz et al. "A Survey of Medical Image Registration", Medical Image Analysis, 2(1): 1-36, Mar. 1998.
Medeiros et al. "Coded Structred Light for 3D-Photography: An Overview", IEEE—RITA, (Latin-American Learning Technologies Journal), IV(2): 109-124, Jul. 1999.
OmniVision "OVM6946 400x400. Compact, Cost-Effective Wafer-Level Camera Module for Single-Use Endoscopes", OmniVision, Product Brief, 2 P., Aug. 10, 2016.
Paperno et al. "A New Method for Magnetic Position and Orientation Tracking", IEEE Transactions on Magnetics, XP011033696, 37(4): 1938-1940, Jul. 2001.
Salvi et al. "Pattern Codification Strategies in Structured Light Systems", Pattern Recognition, 37(4): 827-849, 2004.
Savarese et al. "3D Reconstruction by Shadow Carving: Theory and Practical Evaluation", International Journal of Computer Vision, 71(3): 305-336, Published Online Jun. 1, 2006.
Toshiba "IK-CT2: 0.7×0.7 mm, 220×220, CMOS", Toshiba Information Systems, Product Sheet, 1 P., Dec. 2016.
Restriction Official Action Dated May 25, 2022 From the US Patent and Trademark Office Re. U.S. Appl. No. 16/628,656. (7 pages).
Official Action Dated Aug. 11, 2022 from US Patent and Trademark Office Re. U.S. Appl. No. 16/628,656. (36 pages).
Supplementary European Search Report and the European Search Opinion Dated Aug. 24, 2022 From the European Patent Office Re. Application No. 20739036.0. (9 Pages).
Notice of Allowance Dated Feb. 13, 2023 from the US Patent and Trademark Office Re. U.S. Appl. No. 16/634,152 (11 pages).
Communication Pursuant to Article 94(3) EPC Dated Jan. 18, 2023 from the European Patent Office Re. Application No. 19211372.8 (7 Pages).
Restriction Official Action Dated Dec. 27, 2022 from the US Patent and Trademark Office Re. U.S. Appl. No. 17/211,640 (4 pages).
Supplementary European Search Report and the European Search Opinion Dated Feb. 2, 2023 from the European Patent Office Re. Application No. 22207979.0 (7 Pages).
Official Action Dated Oct. 26, 2022 from the US Patent and Trademark Office Re. U.S. Appl. No. 16/634,152. (15 pages).
Final Official Action Dated Nov. 9, 2021 from US Patent and Trademark Office Re. U.S. Appl. No. 15/274,756. (15 pages).

(56) References Cited

OTHER PUBLICATIONS

Notice of Allowance Dated Nov. 9, 2022 from the US Patent and Trademark Office Re. U.S. Appl. No. 15/274,756. (8 pages).
Official Action Dated Jun. 17, 2021 from the US Patent and Trademark Office Re. U.S. Appl. No. 15/274,756. (16 pages).
Official Action Dated Jul. 20, 2022 from US Patent and Trademark Office Re. U.S. Appl. No. 15/274,756. (25 pages).
Requisition by the Examiner Dated Apr. 7, 2021 From the Innovation, Science and Economic Development Canada, Canadian Intellectual Property Office Re. Application No. 2,896,210. (16 Pages).
Communication Pursuant to Article 94(3) EPC Dated Mar. 10, 2023 From the European Patent Office Re. Application No. 17780530.6 (3 Pages).
Communication Pursuant to Article 94(3) EPC Dated Apr. 25, 2024 From the European Patent Office Re. Application No. 22207979.0 (5 Pages).
Decision to Refuse a European Patent Application Dated Oct. 18, 2022 From the European Patent Office Re. Application No. 18769813.9. (15 Pages).
Interview Summary Dated Nov. 15, 2022 from the US Patent and Trademark Office Re. U.S. Appl. No. 16/645,803. (2 pages).
Kolte et al. "Dimensional Influence of Interproximal Areas on Existence of Interdental Papillae", Journal of Periodontology, 85(6): 795-801, Jun. 1, 2014.
Logozzo et al. "A Comparative Analysis of Intraoral 3d Digital Scanners For Restorative Dentistry", the internet Journal of Medical Technology, 5(1): 1-18, XP055438348, Jan. 1, 2008.
Notice of Allowance Dated Mar. 7, 2023 from the US Patent and Trademark Office Re. U.S. Appl. No. 16/331,974. (14 pages).
Notice of Allowance Dated Dec. 11, 2023 from the US Patent and Trademark Office Re. U.S. Appl. No. 17/211,640. (11 pages).
Notice of Allowance Dated Jan. 24, 2025 from the US Patent and Trademark Office Re. U.S. Appl. No. 16/645,803. (18 pages).
Official Action Dated Jul. 7, 2024 from the US Patent and Trademark Office Re. U.S. Appl. No. 18/198,214. (46 pages).
Official Action Dated Oct. 13, 2022 From the US Patent and Trademark Office Re. U.S. Appl. No. 16/331,974. (83 Pages).
Official Action Dated Jul. 17, 2024 from the US Patent and Trademark Office Re. U.S. Appl. No. 17/422,115. (28 pages).
Official Action Dated Dec. 19, 2023 from the US Patent and Trademark Office Re. U.S. Appl. No. 17/422,115. (61 pages).
Official Action Dated Aug. 23, 2023 from the US Patent and Trademark Office Re. U.S. Appl. No. 16/645,803. (18 pages).
Official Action Dated May 23, 2024 from the US Patent and Trademark Office Re. U.S. Appl. No. 16/645,803. (5 pages).
Official Action Dated Sep. 27, 2022 from US Patent and Trademark Office Re. U.S. Appl. No. 16/645,803. (76 pages).
Official Action Dated Jan. 29, 2025 from the US Patent and Trademark Office Re. U.S. Appl. No. 17/422,115. (6 pages).
Provision of the Minutes in Accordance With Rule 124(4) EPC Dated Oct. 12, 2022 From the European Patent Office Re. Application No. 18769813.9. (11 Pages).
Restriction Official Action Dated May 3, 2022 from US Patent and Trademark Office Re. U.S. Appl. No. 16/645,803. (7 pages).
Restriction Official Action Dated May 17, 2022 from US Patent and Trademark Office Re. U.S. Appl. No. 16/331,974. (10 pages).
Summons to Attend Oral Proceedings Pursuant to Rule 115(1) EPC Dated Jun. 5, 2024 From the European Patent Office Re. Application No. 19211372.8. (10 Pages).
Supplementary European Search Report and the European Search Opinion Dated Jan. 20, 2025 From the European Patent Office Re. Application No. 24208719.5. (8 Pages).
Supplementary European Search Report and the European Search Opinion Dated Feb. 7, 2023 From the European Patent Office Re. Application No. 22213874.5. (11 Pages).
Two Month Non-Extendable Official Action Dated Oct. 31, 2024 from US Patent and Trademark Office Re. U.S. Appl. No. 16/645,803. (2 pages).
Communication Pursuant to Article 94(3) EPC Dated Dec. 17, 2025 From the European Patent Office Re. Application No. 17707964.7 (5 Pages).
Notice of Allowance Dated Nov. 20, 2025 from the US Patent and Trademark Office Re. U.S. Appl. No. 18/107,974. (10 Pages).

* cited by examiner 152
134
138
144
184
128
160
180
140
148
150
164
120
190
124
134
102
184
140
100

152
134
154
128
144
210
212
180
140
148
150
204
164
200
120
124
100
160

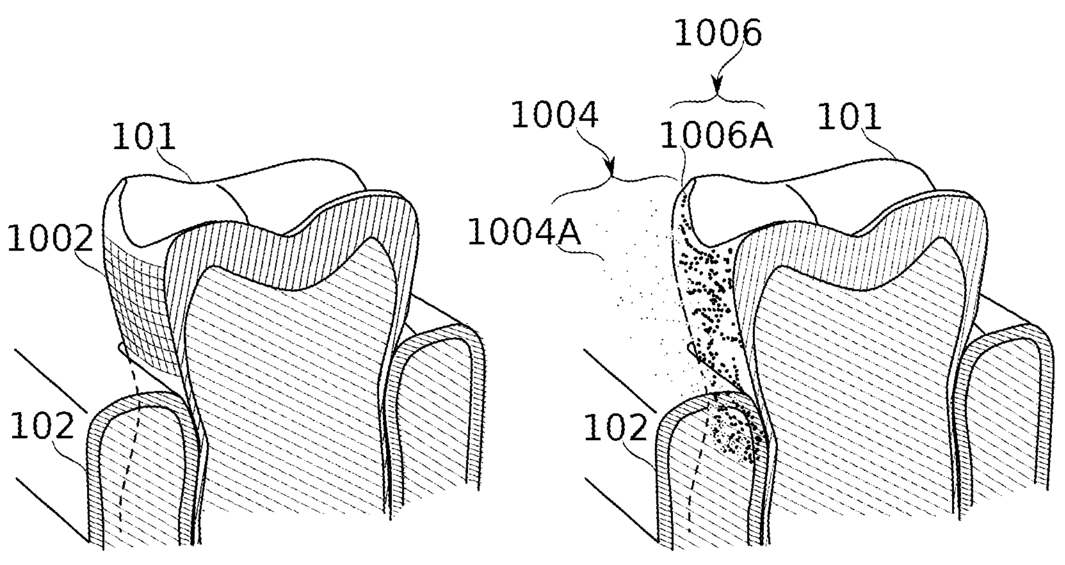
FIG. 10A
FIG. 10B
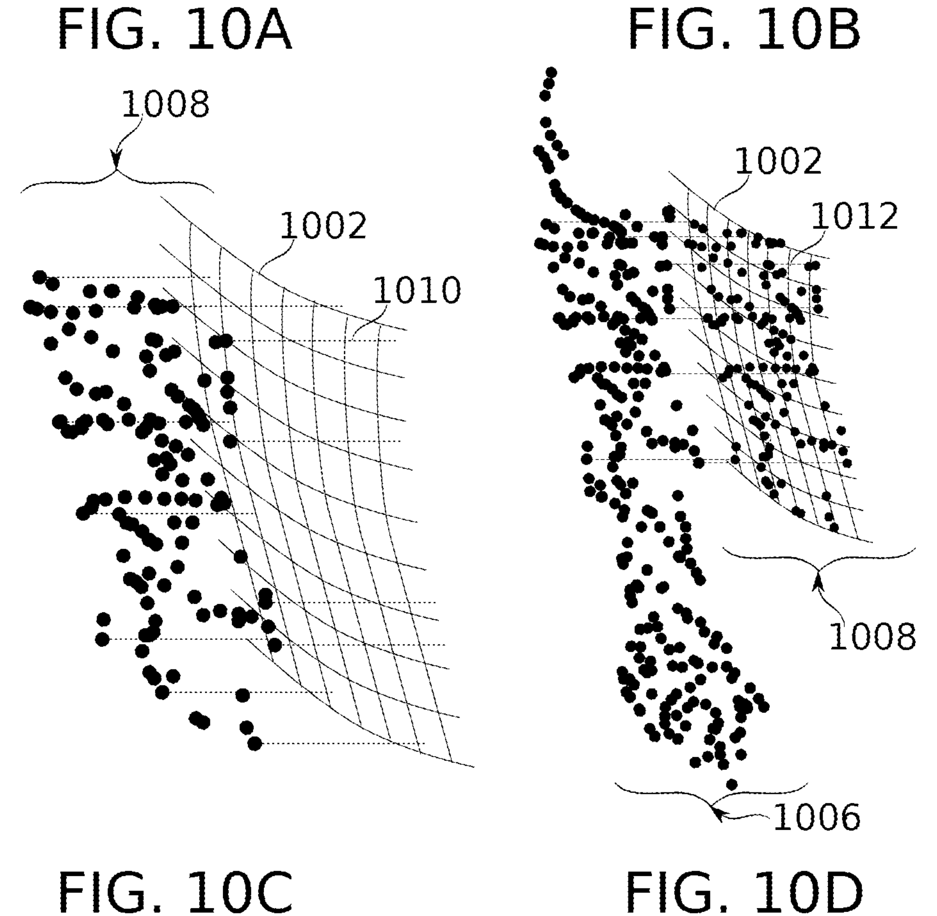
FIG. 10C
FIG. 10D

1102
Optical scan of oral geometry
1104
Bur tip tracking data
1113
Register tracking contours to optical contours
1114
Registered bur tip tracking data 100
124
120
128
130
134
138
144
154
152
160
1202
140
148
150
254

SYSTEM, DEVICE AND METHODS FOR DENTAL DIGITAL IMPRESSIONS

RELATED APPLICATIONS

This application is a continuation of Ser. No. 16/227,995, entitled "System, Device and Methods for Dental Digital Impressions", filed Dec. 20, 2018, which is a continuation Ser. No. 15/571,231, entitled "System, Device and Methods for Dental Digital Impressions", filed Nov. 1, 2017, which is a PCT national stage application of, entitled to, and hereby claiming priority under 35 U.S.C. §§ 365 and 371, corresponding PCT application no. PCT/IL2016/050449, filed May 1, 2016, entitled "System, Device and Methods for Dental Digital Impressions", which claims the benefit of priority under 35 USC § 119 (e) of U.S. Provisional Patent Application No. 62/155,521 filed May 1, 2015; the contents of each of the forgoing is incorporated herein by reference in its entirety.

FIELD AND BACKGROUND OF THE INVENTION

The present invention, in some embodiments thereof, relates to the field of dental digital impressions and more particularly, to techniques, methods, systems and/or devices for the taking of digital impressions.

Certain dental procedures, for example in dental restoration and cosmetic dentistry, include full or partial arch treatment. Teeth restorations include, for example, crowns, inlays, implants, laminates, bridges, prosthesis and/or dentures, fitted to the dental arch.

Traditionally, preparation for dental restoration or other dental treatments commences with drilling and grinding of teeth before preparation of the restoration itself. Optionally, as part of preparation, the gingiva surrounding the tooth crown base is separated from the tooth by use of designated dental tools, and/or use of a cord in a "cord packing" procedure to expose the subgingival tooth portion to view. The separation procedure is potentially invasive and painful.

Optionally, the fully exposed tooth crown is measured using a traditional dental impression, and/or by taking a digital impression with an intra-oral scanner (IOS) to construct a three dimensional (3-D) model of the tooth, teeth or oral arch. The 3-D model is used for producing the required restorations (for example, crowns, inlays, implants, laminates, bridges, prosthesis and/or dentures). The production can be performed by a dental service provider, such as a dental lab; and/or in the dentist's clinic, using, for example, a chair-side milling machine and/or 3-D printer.

SUMMARY OF THE INVENTION

There is provided, in accordance with some exemplary embodiments, a method of tracking a dental tool within an oral cavity, comprising: sensing a sensor-relative position of at least one region of a dental tool via a sensor; and determining an intra-oral position of a rotating dental tool portion based on the sensor-relative position of the at least one region; wherein: the at least one region of the dental tool is configured to move in coordination with the rotating dental tool portion, the rotating dental portion is adapted to contact at least one of a bone surface and tooth surface for preparation thereof, and the sensor is arranged within a range of 5 cm from the at least one region.

According to some embodiments, the rotating dental tool portion is flexibly coupled to a handle of the dental tool.

According to some embodiments, the method further comprises registering the intra-oral position of the rotating dental tool portion to a corresponding position of a representation of a part of a mouth.

According to some embodiments, at least a part of the representation of a part of a mouth is a representation derived from an optical oral scan.

According to some embodiments, the preparation comprises removing material from the at least one of a bone surface and tooth surface, and the intra-oral position is located within the volume of the removed material.

According to some embodiments, the rotating dental tool portion is positioned sub-gingivally.

According to some embodiments, the sensor comprises a magnetic sensor.

According to some embodiments, the at least one region comprises a magnetic marker.

According to some embodiments, the magnetic marker is configured to produce a time-varying magnetic field.

According to some embodiments, the sensing further comprises sensing a plurality of the regions of the dental tool simultaneously, and wherein the determining comprises determining the relative positions of the plurality of the regions.

According to some embodiments, the at least one region is offset from the rotating dental tool portion, and wherein the determining is also based on the offset.

According to some embodiments, the offset comprises a variable offset angle between the at least one region and the rotating dental tool portion, relative to the part of the mouth, and wherein the method further comprises sensing of the offset angle.

According to some embodiments, the intra-oral position comprises a 3-D orientation of a longitudinal axis of the rotating dental tool portion.

According to some embodiments, the at least one region is configured to rotate with the rotation of the rotating dental tool.

According to some embodiments, rotation of the at least one region activates the at least one region for sensing.

According to some embodiments, the determining comprises calculating a 3-D volumetric extent of the rotating dental tool portion based on a modeled surface of the rotating dental tool.

According to some embodiments, the sensor is intra-orally located.

According to some embodiments, the sensor is located on a handle of the dental tool.

There is provided, in accordance with some exemplary embodiments, an intra-oral position tracking system, comprising a drill tool including a bur with a portion comprising a magnet.

According to some embodiments, the system further comprises a sensor configured to sense a relative position of the magnet portion, within a range of 5 cm, and to an accuracy within at least 0.5 mm in three dimensions.

According to some embodiments, the sensor is configured to be detachably affixed within an oral cavity.

According to some embodiments, the system further comprises a processor configured to calculate: a position of a preparing portion of the drill tool for preparing at least one of a bone and a tooth, based on the sensed relative position, and a geometrical location of the magnet portion relative to the preparing portion.

According to some embodiments, the processor is further configured to calculate the position of the preparing portion based on an estimate of oral geometry in the vicinity of the preparing portion.

There is provided, in accordance with some exemplary embodiments, a dental impression system, comprising: a drill tool including a preparing portion for preparing at least one of a bone and a tooth; an optical sensor positioned to optically sense a geometry of the preparing portion; and a processor configured to calculate a volume of the preparing portion, based on the optically sensed geometry.

According to some embodiments, the optical sensor comprises a camera positioned on the drill tool to view the preparing portion.

According to some embodiments, the system further comprises a pulsed water jet source configured for cooling the preparing portion, wherein the optical sensor is synchronized to sense the geometry between water jet pulses from the pulsed water jet source.

According to some embodiments, the processor is further configured to calculate a geometry of a prepared surface of, based on the measured position and the calculated volume of the preparing portion.

According to some embodiments, the position tracker comprises a camera positioned to image positions of the preparing portion relative to intra-oral features, and is configured to measure position of the drill tool preparing portion based on the imaged relative positions.

According to some embodiments, the camera positioned to image positions of the preparing portion relative to intra-oral features comprises a 3-D camera.

According to some embodiments, the preparing portion is coupled to a magnetic portion configured to produce a magnetic field, and wherein the position tracker measures position of the preparing portion based on measurement of a position-varying parameter of the magnetic field by a magnetic sensor.

According to some embodiments, the magnetic field is rotating, and wherein the position-varying parameter of the magnetic field comprises a time-varying profile of magnetic field intensity at the position of the magnetic sensor.

According to some embodiments, the system further comprises a force sensor configured to sense lateral forces applied to the preparing portion.

According to some embodiments, the position tracker is further configured to distinguish positions at which the preparing portion makes contact with the oral geometry, based on the sensed lateral forces.

According to some embodiments, the system further comprises an orientation sensor configured to sense an orientation of the drill tool, wherein the position tracker is further configured to calculate the position of the preparing portion based on the sensed orientation.

According to some embodiments, the position tracker is further configured to calculate the position of the preparing portion based on the sensed lateral deflection.

There is provided, in accordance with some exemplary embodiments, a method of calibrating output of a position-sensing system to the geometry of an oral surface, comprising: receiving a 3-D model of the oral surface; tracking positions of a probe volume of the position-sensing system, including positions in which the probe volume approaches the oral surface; registering the tracked positions to the 3-D model of the oral surface based on a mapping between a surface at which encounters of the probe with the oral surface limit motion of the probe, and the 3-D model of the oral surface.

According to some embodiments, the registering comprises determining a transform between the tracked positions and the 3-D model of the oral surface, and wherein the method further comprises registering tracked positions away from the modeled oral surface, based on the transform.

There is provided, in accordance with some exemplary embodiments, a method of calibrating a position-tracking system probe position within a mouth, comprising: optically sensing a portion of the position-sensing system in contact with an oral surface, as well as a surrounding portion of the oral surface, while separately obtaining position tracking data for the probe; and registering the separately obtained position tracking data to a 3-D model of the oral surface, based on registration of the optically sensed data to the 3-D model of the oral surface.

There is provided, in accordance with some exemplary embodiments, a dental tool, comprising a dental bur having at least one optical fiber placed within the bur.

According to some embodiments, the tool further comprises: an optical sensor configured to sense light returned through the optical fiber from at least one light inlet of the optical fiber; and a processor configured to characterize a region of the placement of the at least one light inlet, based on at least one light level detected by the optical sensor.

According to some embodiments, the at least one light inlet includes a light inlet positioned at a distal end of the bur, and wherein the characterizing comprises determining a sub-gingival position of the distal end.

According to some embodiments, the at least one light level comprises a plurality of light levels corresponding to a plurality of light wavelength ranges, and wherein the region of placement is characterized based on the relative values of the plurality of light levels.

According to some embodiments, the at least one light inlet comprises a plurality of light inlets distributed along the bur.

According to some embodiments, the processor is additionally configured to change the operation of the dental tool, based on the characterization of the region of placement.

According to some embodiments, the change in operation comprises a change in rotational speed of the bur.

According to some embodiments, the change in operation comprises limitation of a period of operation of the dental tool.

According to some embodiments, the tool further comprises a light source coupled to deliver light through the at least one optical fiber.

According to an aspect of some embodiments of the present invention, there is provided a dental digital impression system for three-dimensional (3-D) measurement of at least one tooth, comprising: a dental drill including a drill bur extending therefrom; a tracking element configured to track a 3-D spatial location of the bur relative to a contour of at least one tooth; and a processor for receiving the tracked 3-D spatial location and processing thereof for translating the tracked location to a measurement of the contour of the at least one tooth.

According to an aspect of some embodiments of the present invention, there is provided a dental digital impression system for three-dimensional measurement of at least one tooth, comprising: a dental drill including a drill bur extending therefrom; a magnet coupled to the bur and configured to create a modulated electromagnetic field; a sensor configured to track a 3D spatial location of the magnet relative to a contour of at least one tooth; and a processor for receiving the tracked 3D spatial location and processing thereof for translating the tracked location to a measurement of the contour of the at least one tooth.

There is thus provided according to some embodiments a dental digital impression system for three dimensional (3-D) measurement of at least one tooth, comprising a dental drill including a drill bur extending therefrom, a magnet placed at the bur and configured to create a modulated electromagnetic field, a sensor configured to track a 3-D spatial location of the magnet relative to a contour of at least one tooth, and a processor for receiving the tracked 3-D spatial location and processing thereof for transforming the tracked location into a measurement of the contour of the at least one tooth. The rotation of the bur may cause the magnet to create the modulated electromagnetic field.

In some embodiments, the system further comprises optical tracking of the oral cavity. The optical tracking may comprise a camera placed on a dental preparation tool or within the dental digital impression system. In some embodiments, at least one optical fiber may be placed within the bur. The optical fiber may detect portions of the oral cavity by its chromatic variations, and/or by another optical property.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 10A schematically shows a mapped contour of a tooth, superimposed on the tooth, according to some embodiments of the present disclosure;

FIG. 10B schematically shows a point cloud comprising drill bur position measurement points in proximity to a tooth, according to some embodiments of the present disclosure;

FIG. 10C schematically indicates relationships between a mapped contour and a subset of position measurements taken from contour-contacting position measurements, according to some embodiments of the present disclosure;

FIG. 10D schematically indicates relationships between the superset of contacting position measurements and the subset of position measurements used in alignment, according to some embodiments of the present disclosure;

DESCRIPTION OF SPECIFIC EMBODIMENTS OF THE INVENTION

Figure 1A:
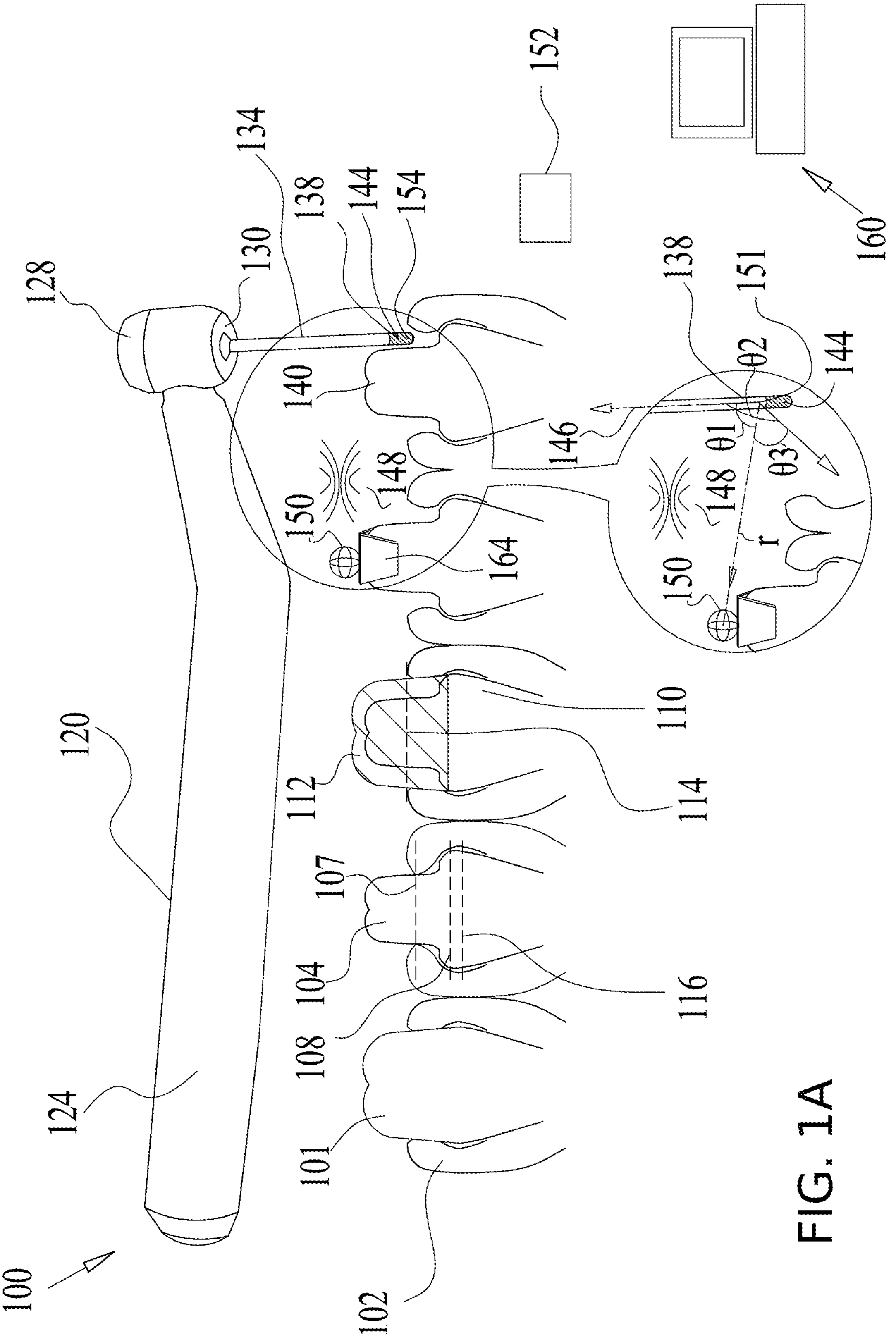
FIGS. 1A-1B are each a simplified schematic illustration of a dental digital impression system using magnetic position sensing, according to some embodiments of the present disclosure.

The present invention, in some embodiments thereof, relates to the field of dental digital impressions and more particularly, to techniques, methods, systems and/or devices for the taking of digital impressions.

Overview

A broad aspect of some embodiments of the current invention relates to systems, devices and/or methods for measurement of supragingival and/or subgingival tooth portions; optionally during drilling/grinding or other tooth material removal steps comprising a dental treatment. In some embodiments, the dental treatment comprises, for example, dental restoration; and/or a cosmetic procedure, such as veneer placement.

An aspect of some embodiments of the current invention relates to dental contour and/or surface sensing based on positions assumed by a dental tool as it is moved in the neighborhood of an oral surface. Optionally, the positions include positions where a portion of the dental tool is in contact with the oral surface. Optionally, the oral surface is subgingival.

In some embodiments, the position of a probe portion of a dental tool (optionally, a portion of a dental bur, for example, a cutting portion of a dental bur) is tracked as it moves within a mouth. In some embodiments, the tracking comprises tracking of a trackable portion of the dental tool which is coupled to a tooth-contacting (and/or other oral geometry contacting) probe portion of the dental tool, such that the two portions move in registry with one another. Optionally, one or both of the probe portion and the trackable portion rotate. In some embodiments, the trackable portion comprises a marker; for example, a magnetic portion which participates in magnetic position sensing via a magnetic position element placed within the oral cavity. For example, in some embodiments, the marker comprises a magnetic field generator coupled to the cutting portion, and the magnetic position element comprises a magnetic sensor. Optionally, the magnetic field generator and the magnetic sensor are reversed in relative position, with the magnet fixed to the jaw, for example as an electromagnet assembly configured to produce a rotating magnetic field when operated; and with the sensor affixed to the dental tool. In some embodiments, the sensor is affixed to the dental tool in a place other than on the dental bur; for example, held within the head and/or handle of the dental tool, or attached thereto by a bracket. Optionally, the sensor is reversibly affixed, replaceable, and/or disposable.

Optionally, the magnetic sensor is configured to determine a relative position of the marker in three dimensions (3-D). Optionally, a distance between a magnetic field generator (e.g., a rotating permanent magnet and/or an arrangement of electromagnetic coils) and a magnetic sensor is, for example, 5 cm or less. Optionally, the distance is up to 10 cm, 7 cm, 5 cm, 4 cm, or another maximum distance. Optionally the magnetic sensor is affixed intraorally; optionally, the maximum distance is a maximum distance between the magnetic sensor and the magnetic field generator while both are intraorally positioned. Optionally, the magnetic sensor is affixed intraorally on the same jaw as the prepared tooth, teeth, and/or bone. Optionally, the magnetic sensor is affixed intraorally on both jaws (e.g., one sensor affixed with both jaws held fixed relative to one another, or a plurality of sensors, with at least one sensor affixed to each jaw). In some embodiments, a trackable portion position (e.g., a marker) is optically sensed. In some embodiments, the trackable portion and the optical sensor are both intraorally positioned. Optionally, the optical sensor is intraorally affixed; for example, with a maximum distance as described for magnetic sensing.

In some embodiments, an oral geometry-contacting portion of a dental tool is flexibly coupled to the dental tool. For example, the mounting of a dental bur allows some angular deflection of the bur, e.g., when the bur is pressed against a tooth and/or bone to grind it. Optionally, the deflection comprises a movement of up to, for example, about 250 μm, 500 μm, 750 μm, 1 mm, 2 mm, or another larger, smaller, or intermediate deflection. In some embodiments of the invention, the trackable portion of the dental tool is deflected along with the oral geometry-contacting portion of the dental tool. Optionally or additionally, deflection of the oral geometry-contacting portion of the dental tool is detected by another sensing method, for example, a defection force sensor.

In some embodiments, as a drill (for example, the probe portion of the drill) follows and/or shapes a contour or other required region or portion of the tooth, a 3-D spatial location of the drill relative to the tooth is measured, traced, tracked, and/or stored. Optionally or additionally, the subgingival tooth portion may be exposed and/or explored by a probe portion such as a bur (or another tool of the drill). Potentially, this obviates the cord packing step for impressions taken by conventional methods or with use of an intra-oral scan (IOS). Potentially, obviating of the cord packing step also reduces the time it takes to obtain a baseline IOS. In some embodiments, an existing map of the shape of the oral geometry is extended and/or updated according to the probe motions (e.g., as tooth material is removed, and/or as the probe moves into oral surface regions which were not previously mapped). In some embodiments, dynamically recording changes in the shape of the oral geometry due to drilling/grinding potentially obviates a need to re-scan the mouth after tooth preparation is complete.

In some embodiments, the drilling itself is monitored, allowing use of a tooth preparation plan to guide the drilling. Optionally, drilling time and/or intensity (e.g., drilling pressure and/or drill rotation rate) are monitored. Optionally, as a preparation plan nears completion in some region, drilling intensity (e.g., drill rotation rate) is automatically reduced.

The tracked measurements can be used, e.g., for guiding tooth preparation; for constructing crowns, bridges, prosthesis and/or dentures for dental restoration; for veneer placement; or for any other dental treatment. In some embodiments, a current status of preparation is displayed, optionally along with indications of the preparation plan itself to allow comparison between current and planned preparation results. Optionally, preparation status is updated in real time based on tracked movements.

Proper structuring of crowns, bridges, prosthesis, veneer and/or dentures is dependent on sufficient accuracy of tooth measurements. In some embodiments, systems track the location of the drill by measuring the location of the drill head, typically housing the drill motor. The drill motor rotates at a relatively high speed, potentially causing the bur of the drill, extending from the drill head, to vibrate and deviate from a fixed relationship with the location of the drill head as the bur touches the tooth. Also, in some dental tools, the rotating portion (e.g., the bur itself, and/or a chuck or other mounting for the bur) allows some relative flexibility and/or tilt relative to the rest of the dental tool. In some embodiments, a bur is flexibly coupled to a dental tool head and/or dental tool handle, such that force applied by pressing the bur against a tooth deviates the bur from its initial orientation relative to the dental tool head and/or handle. Accordingly, tracking the drill head to measure the contour of the tooth potentially suffers from inaccuracies, due to the deviation and tolerances of the bur relative to the drill head (or any other location on the drill). The current tolerance of the bur relative to the drill head is, for example, in the range of about 200-500 μm.

In some embodiments of the present disclosure, the bur is directly tracked as it contacts and traces the contour of the tooth at the supragingival and/or the subgingival tooth portions, for example, tracked relative to a fixed portion of the drill head, and/or separately traced. Optionally, tracking to determine a surface does not require specifically distinguishing contact; for example, the surface is considered to be implied by a boundary of a complementary space into which a volume of the bur does not intrude. According to some embodiments of the present disclosure, this increases accuracy and reduces tolerance errors due to movement of the bur relative the drill head to less than 200 μm: for example, within the range of 30-100 μm or within the range of 30-200 μm.

In some embodiments, the distance between a tracked marker and a sensor used in the position tracking of a dental tool is less than or equal to about, for example, 10 cm, 7 cm, 5 cm, 4 cm, 3 cm, 2 cm, 1 cm, or another larger, smaller, or intermediate distance.

In some embodiments of the invention, one or more auxiliary tracking sensors are used to track the movement of a tooth-contacting portion of the dental tool. In some embodiments, an orientation sensor is used, for example, to track the general orientation of a dental tool, such as the handle of a dental tool.

For example, the orientation is measured using a gyro, an accelerometer to measure the direction of the gravity, and/or a magnetic compass to measure the direction to the earth magnetic field. Optionally, one or more such sensors are implemented, for example, in a small chip. In some embodiments, a relative displacement between two or more portions of a tracked dental tool is determined. For example, the orientation of a marker coupled to a dental bur is measured relative to the handle of a dental tool by use of a force sensor, angular encoder, and/or other sensor for producing position data.

An aspect of some embodiments of the current invention relates to dental contour (e.g., surface and/or volume position) updating based on the determination of positions where a non- and/or indirect-contact dental preparation tool ablates and/or otherwise prepares a surface of an oral geometry. In some embodiments, the updating is of an existing map of an oral geometry surface.

In some embodiments, a dental procedure is performed by use of a preparation tool which does not directly touch the tooth (herein, a "projecting preparation tool"). For example, one or more lasers are used to remove tooth portions. Additionally or alternatively, a projecting preparation tool uses water jets, alumina blasting, or another medium to projects material and/or energy to the tooth.

In some embodiments, the projection source position (relative to the oral geometry) and/or projection direction (e.g., of a treating laser beam and/or jet) is determined, e.g., based on sensors encoding the position and/or orientation of the projecting preparation tool. From this information, a treated oral surface region at which the beam and/or jet intersects with a targeted oral geometry is determined. Optionally, removed portions of the teeth are estimated; based for example, on the time and/or intensity of treatment at each treated oral surface, and/or on known and/or estimated ablative properties of the tooth material itself. Optionally, a new contour of the teeth is derived from the removed portion estimate.

In some embodiments, the system is configured to stop treatment when treatment-excluded areas in the oral cavity are targeted by the projection source position and/or orientation. Areas are optionally treatment-excluded, for example, due to previous removal of overlying material, due to a sufficient degree of treatment having already been performed, and/or due to the area being away from an area which is to receive any treatment at all. Optionally, the system is configured to modulate projected treatment (e.g., a beam and/or jet) according to a targeting plan and/or according to the material targeted (e.g., to reduce a power of a laser and/or jet). Optionally, when treatment-excluded areas are targeted, an alert is generated to the physician.

An aspect of some embodiments of the current invention relates to use of optical measurements for assessment of material (for example, composition and/or structure) receiving treatment. In some embodiments, probe light is delivered by optical fiber to an outlet on a portion of a dental tool which is directly involved in material preparation, e.g., via a fiber which runs through and/or along a dental bur and comprises one or more outlets. In some embodiments, probe light is delivered by a remote light source. In some embodiments, probe light is collected by an optical fiber running through and/or along a dental bur, and having at least one inlet. Optionally, material assessment comprises spectrographic analysis of sampled probe light (for example, relative intensities of light frequencies passing through different materials are differentially affected by different materials). Optionally, material assessment comprises analysis of probe light intensity (for example, an amount of sampled light indicates a degree of sampling input proximity to an illuminated material, a degree of light scattering by a material, and/or a degree of light absorbed by a material.

Optionally, operation of a device is selected and/or modulated according to the assessment of the material. In some embodiments, a drill operation parameter (e.g., speed) is selected according to the contacted material; for example, in order to equalize a rate of material removal among different materials, and/or to reduce a rate of removal upon reaching a particular material layer and/or thickness thereof. In some embodiments, a laser device is used in material preparation, and a laser operation policy (e.g. direction, power, and/or pulse application) is selected.

An aspect of some embodiments of the current invention relates to contour comparison-based calibration of probe position tracking data to a model representing the oral geometry; for example, a model which is used in the design of an artificial dental fixture.

In some embodiments, an optical oral scan or other oral geometry data is provided, on the basis of which an oral geometry model is produced. In some embodiments, the oral geometry model is incomplete (for example, subgingival tooth contours) and/or subject to modification during dental work (for example, by drilling and/or grinding using a dental tool). In some embodiments, the extension and/or updating of the dental model relies on a calibration, which describes how relative position measurements should be transformed into the spatial coordinate system of the model.

In some embodiments of the invention, calibration comprises comparison to match shapes of contours found in both an original model and in updating data. Additionally or alternatively, In some embodiments, calibration comprises matching of a sensed contact position (for example, a position sensed by magnetic field-based detection of a magnetic marker) to an oral geometry model, based on an optical scan of a portion of a dental drill in situ against a background comprising a region modeled by the oral geometry model. Optionally, calibration comprises use of data from an orientation sensor coupled to an orientation of the dental tool.

Herein, descriptions pertain to a single tooth. However, it should be understood that the method of the present disclosure can be applied, changed as necessary, for a plurality of teeth, for any location or area within the dental arch, and/or for preparation of bone (e.g. jawbone). It is further noted that measurement of the contour may include a 3-D measurement of some or all surfaces of the tooth.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Figure 1B:
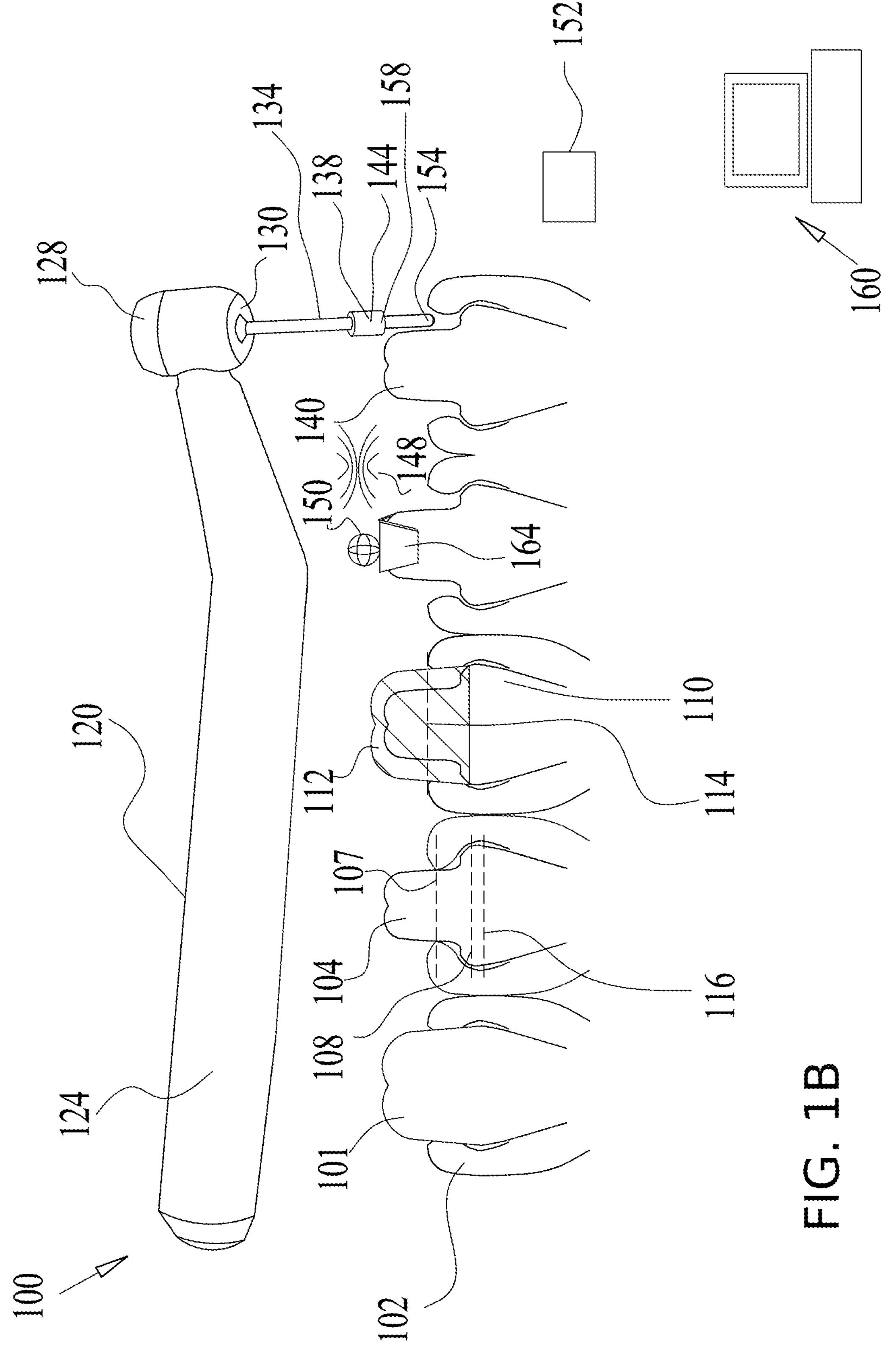

Reference is now made to FIGS. 1A and 1B, which are each a simplified schematic illustration of a dental digital impression system 100 using magnetic position sensing, according to some embodiments of the present disclosure.

In FIGS. 1A and 1B, an exemplary untreated tooth 101 is shown with surrounding gingiva 102. Prepared tooth 104 depicts a drilled tooth which has been subjected to initial tooth preparation, as described above. As can be seen in FIGS. 1A and 1B, showing the tooth preparation with a subgingival finishing line, only a supragingival tooth portion at the coronal side of (or above) a gum line 107 is visually exposed for digital impression, standard impression or other tooth measurements techniques, without performing invasive procedures revealing the subgingival regions, e.g., cord packing. A preparation finishing line 108 delineates the border between a prepared tooth portion in the coronal direction (above) and a natural tooth portion in the apical direction (below). Preparation finishing line 108 separates between the natural tooth which occasionally includes the tooth enamel coating and the prepared tooth from which the enamel has generally been removed. A subgingival preparation area is the tooth area apical of (below) gum line 107 and continues apically towards the finishing line 108 and includes a subgingival preparation margin. Generally, but not necessarily, the preparation margin has a step like shape. In some cases the step shape can be rounded or can have any shape suitable for the clinical situation.

Generally, a well-fitting crown or bridge covers substantially all portions of the tooth which have been shaped or prepared (e.g., by drilling), for example, the tooth portions coronal to or above preparation finishing line 108. In some embodiments, for construction of a prosthetic or crown which properly fits the prepared tooth, measurements of tooth subgingival area should (or may) have an accuracy of around 30 μm, but in some cases may have an accuracy of about 200 μm or about 100 μm or about 30 μm or about 10 μm or within the range of 10-200 μm, or a range of greater accuracies. A reason for covering all prepared areas of the tooth with the crown is that during preparation, tooth enamel is removed, leaving uncovered portions vulnerable to decay. A further reason is to provide structural durability to the restored tooth.

Tooth 110 depicts a crowned tooth showing a crown 112 which has been affixed (usually cemented) over prepared tooth 104. Gingiva 102 meets the crown at the free gingival line 114. Typically, crown 112 restores the general shape of the original tooth. Crown 112 is optionally a well-fitting crown with a smooth area between the apical edge of the crown and the finishing line of the preparation 108, allowing close-fitted installation. A smooth surface junction between the prosthesis and the natural tooth is often desirable as preventing crevices or mis-fittings at the finish line 108. A poor (e.g., gapped) fit of the crown-tooth junction at the finishing line area can provide a hospitable environment for bacteria. Bacteria potentially cause gum inflammation, tooth decay and eventually may lead to a need to replace the restoration or even to tooth loss. There are many reasons to place the finishing line 108 apical to the free gingival line 114, for example: aesthetic reasons (color difference or visible junction between the natural tooth and a prosthesis), covering of preexisting restorations (e.g. fillings) or covering of preexisting decay which extends beneath the gum line, and/or to provide enough retention surface for the crown.

For modeling to achieve this fit, it is generally desirable to record the emergence profile of the tooth/teeth apically to the finishing line 108. This inclination (slope, gradient) is optionally used in designing the surface of the crown. In some embodiments (e.g., in order to match the crown/prosthetic inclination with the natural tooth inclination), the 3-D surface dimensions of the tooth portion below finish line 108 (shown by line 116), are measured to approximately 0.5 mm-1 mm below (in the apical direction of) preparation finish line 108. Optionally, the measurement is to about 0.1 mm-5 mm beyond preparation finish line 108.

In some embodiments, the dental digital impression system 100 comprises a dental drill (dental drilling handpiece) 120 including a handpiece 124 and a head portion 128. From an oral-facing surface 130 of the head portion 128 extends a drill bur 134. In some embodiments, a tracking element 138 is provided at any suitable location for tracking the movement of the bur 134 relative to any tooth 140, relative to a known reference location in the oral cavity, and/or relative to the drill 120, for example relative to head portion 128.

In some embodiments, the tracking of the bur 134 is by electromagnetic tracking methods. Optionally, at least one permanent magnet 144 is located at bur 134; oriented, for example, such that its magnetic axis is generally perpendicular to bur rotation axis 146 at the bur surface, as shown in the insert of FIG. 1A. Additionally or alternatively, revolutions of the bur 134 during operation of the drill 120 also rotate magnet 144 for creating a modulated electromagnetic field 148. In some embodiments, the revolutions of the magnet 144 create the modulated electromagnetic field 148 with no need to for supplying an AC current.

In some embodiments, magnet 144 comprises an electromagnet that is excited with modulated current. Optionally, the current is modulated by induction from an electromagnetic field emitted from head portion 128 or another location. In some embodiments, magnet 144 is an electromagnet in which current is excited by wires communicating, e.g., with head portion 128.

Optionally, tracking is performed by an electromagnetic field sensor 150, formed in any suitable manner. In some embodiments, the sensor 150 comprises a sensing coil. In a non-limiting example, the sensor 150 comprises a singular or plurality of (e.g. two or three) concentric, orthogonal coils. In some embodiments, sensor 150 comprises one or more MEMS-based (small scale microelectromechanical) sensors, optionally placed at orthogonal directions. A potential advantage of using multiple sensing axes is to allow disambiguation of field data received at a single sensing axis. For example, a one-axis sensor may be unable to distinguish between a more distant magnet positioned on-axis, or a closer magnet positioned off-axis. Combined with readings from a second, substantially orthogonal electromagnetic sensor, position ambiguity within a plane may be resolved; combined with a third electromagnetic sensor, substantially orthogonal to the first two, position ambiguity in space may be resolved.

Optionally, sensor 150 is configured to be placed and fixed during preparation to at least one tooth 140, at any suitable location for tracking (within the modulated electromagnetic field 148) the 3-D spatial location (e.g. the distance and angle) of the bur 134 relative to the sensor 150. Additionally or alternatively, sensor 150 is mounted on the body of the drill 120 itself. Optionally, sensor 150 is mounted on the body of the drill temporarily, for example as an add-on (e.g., using an external bracket), sensor 150 mounted to the drill handle. A handle-mounted sensor optionally measures movement of magnet 144 relative to the drill 120, which can be combined with another measurement of drill position (e.g., by optical, magnetic, inertial, and/or other sensing) in order to account for relative movements, e.g., due to flexing and/or wobble.

Optionally, a modulated electromagnetic field 148 is induced by rotating the magnet 144, such as by the rotation of the bur 134. Optionally, the poles of magnet 144 are pointed off of the rotational axis of bur 134; for example, orthogonal to the rotational axis. Optionally, rotation of the magnet (and/or of the field it produces) provides a time-cyclic signature from which information such as amplitude and phase can be used to determine the relative position of magnetic field source and sensor. Optionally, modulation of the magnetic field is used to produce a frequency which can be distinguished from potential sources of electromagnetic interference at other frequencies (optionally including DC frequency). A method of magnetic position detection by use of a magnetic field generated from a crossed coil pair (driven to produce a rotating field similar in effect to a rotating permanent magnet) is described, for example, by Paperno et al. (*A New Method for Magnetic Position and Orientation Tracking*, IEEE TRANSACTIONS ON MAGNETICS (2001), 37:4; 1938-1940). Optionally, positional interpretation of electromagnetic field measurements includes consideration of information about the orientation of magnet 144 and/or its field over time. This may be provided, for example, by a bur position encoder in the drill head 128, and/or by generating the field in a known phase relationship to field measurement timing. Additionally or alternatively, one or more alternatives for resolving ambiguous position data (e.g., data consistent with more than one alternative position) are rejected for being geometrically unreasonable (e.g., inconsistent with known oral geometry and/or the movement history of the bur).

The 3-D spatial contour traveled by the magnet 144 (and accordingly bur 134, suitably adjusted for any significant offset) is optionally calculated by consideration of the changing relative position of sensor 150 within a coordinate system 151. An exemplar of a coordinate system 151 shown in FIG. 1A is defined, for example, according to a distance r and at least one of the angles $\theta_1$, $\theta_2$, and $\theta_3$ from a coordinate origin, such as at the magnet location, as seen in the insert of FIG. 1A. In some embodiments, angles are measured relative to sensor 150. In some embodiments, angles of magnet 144 relative to sensor 150 are measured; optionally additionally or alternatively to angles $\theta_1$, $\theta_2$, and $\theta_3$ of bur 134 relative to sensor 150. Optionally, angle $\theta_3$ is measured by analysis of the temporal phase of a magnetic field, obtained, for example, by synchronizing bur 134 rotation with magnetic field measurement at sensor 150.

In some embodiments, a coordinate system comprises a distance r and two angular measures such as azimuth and angular altitude (e.g., $\theta_3$ is a measure of azimuth, and $\theta_1$, is a measure of angular altitude). In some embodiments, a coordinate system comprises measurements of distance x, y, z, along each of three orthogonal axes (for example, rotational axis 146 and two other axes mutually orthogonal to each other and to rotational axis 146). Additionally or alternatively, the coordinate system is defined by the sensor 150, by another landmark in the mouth, and/or by a combination of several landmarks (e.g., a center of mass of their positions).

The relative location of the magnet 144 as measured by sensor 150 is optionally transmitted by a wired or wireless transmitter 152 to a processor 160 (transmitter 152 in turn is in wired or wireless communication with sensor 150 so as to receive location measurement data therefrom). Optionally, processor 160 is configured as a movement tracker, to receive the tracked location of the magnet 144, and/or to receive data indicating the tracked location of the magnet 144 and convert it into positions and/or movements. In some embodiments, processor 160 is also configured for processing to translate the tracked location of magnet 144 (suitably adjusted for its relationship to the geometry of bur 134) into a measurement of the contour of tooth 140 which bur 134 follows. It should be understood that the location of bur 134 (optionally a specific portion of bur 134 such as an outermost contact point) is optionally determined by factoring in a known offset from the position of magnet 144, and/or a known volume of bur 134. Optionally, the offset is sufficiently small that slight angular deviations due to deflection and/or angle of drill orientation are negligible to the accuracy of the results. Optionally, supplementary angular information is provided, for example, by measuring an orientation of the drill 120, a position of head portion 128, or another position, for example by optical, magnetic, or other means. Optionally, supplementary angular information is provided by directly or indirectly measuring deflection of bur 134 relative to head 128; for example as described herein in relation to FIG. 5. Optionally, a change in the magnetic field pattern encodes partial information of the contact angle, by specific structure of the magnet 144 (e.g., use of two magnetic portions detected at different rotational phases).

Figure 1C:
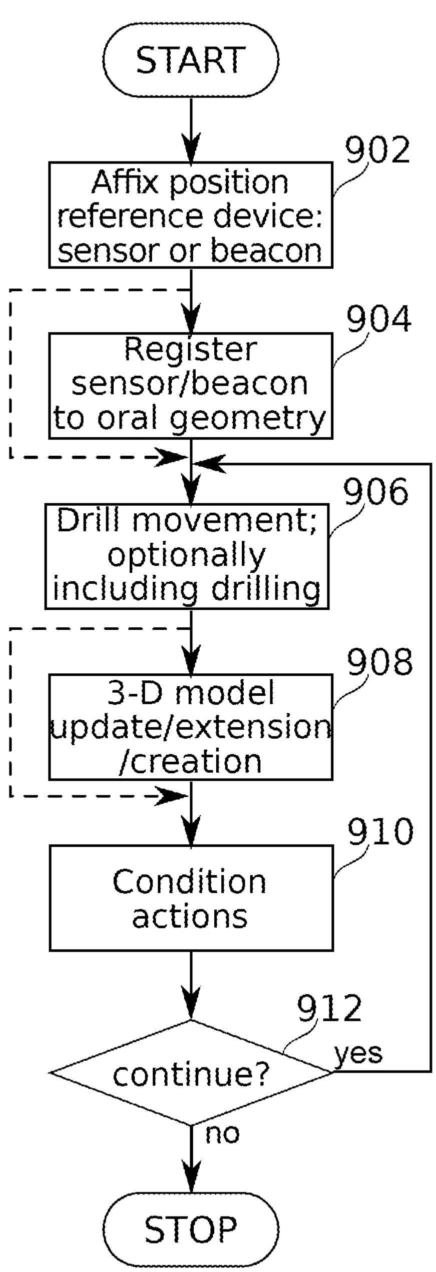
FIG. 1C is a schematic flowchart of a method of tracking the position of a drill bur, according to some exemplary embodiments of the present disclosure.
Figures 2A, 2B:
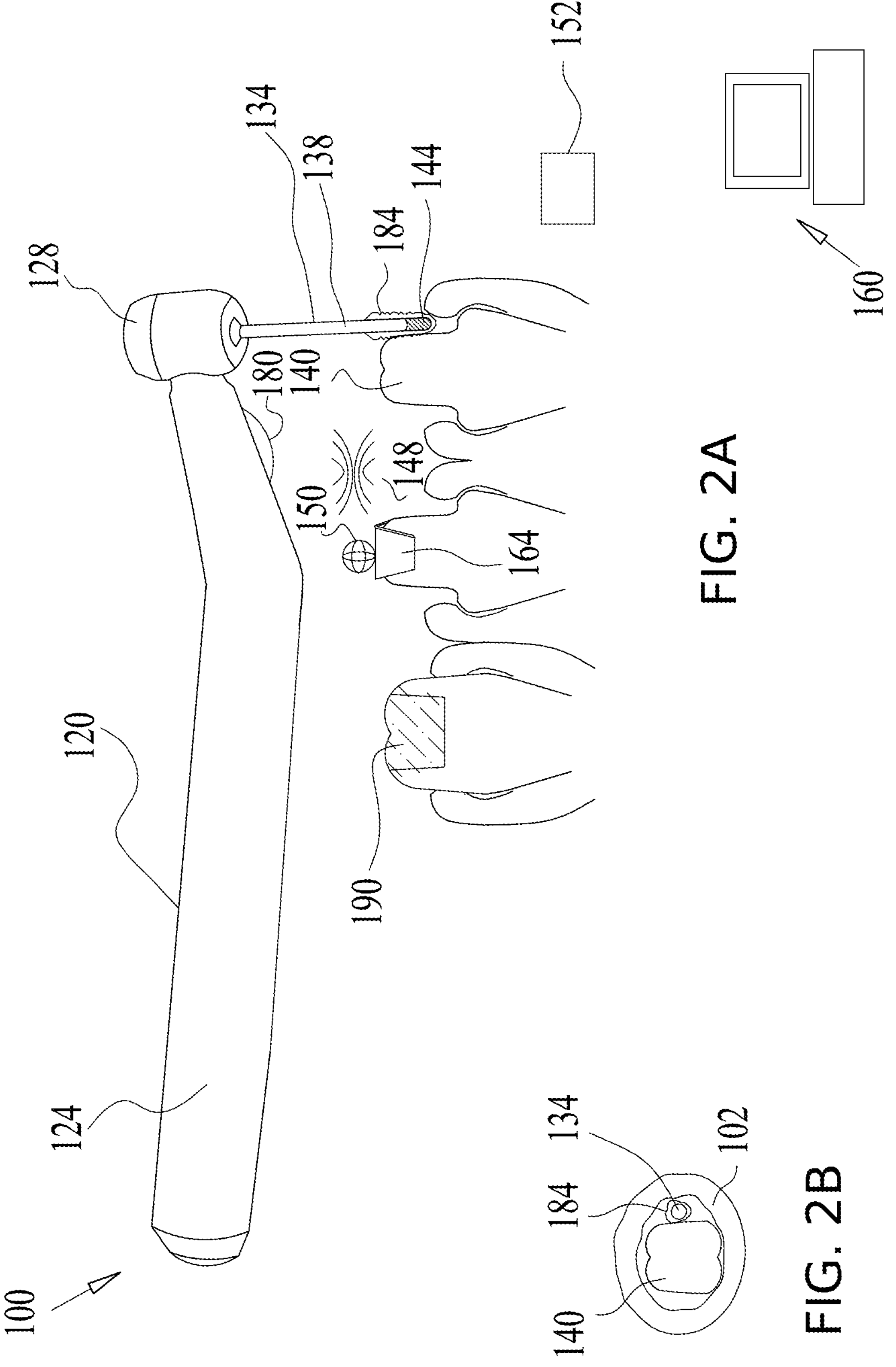
FIGS. 2A-2B are simplified schematic illustrations of a dental digital impression system comprising magnetic and optical position sensing, according to some embodiments of the present disclosure.
Figure 3:
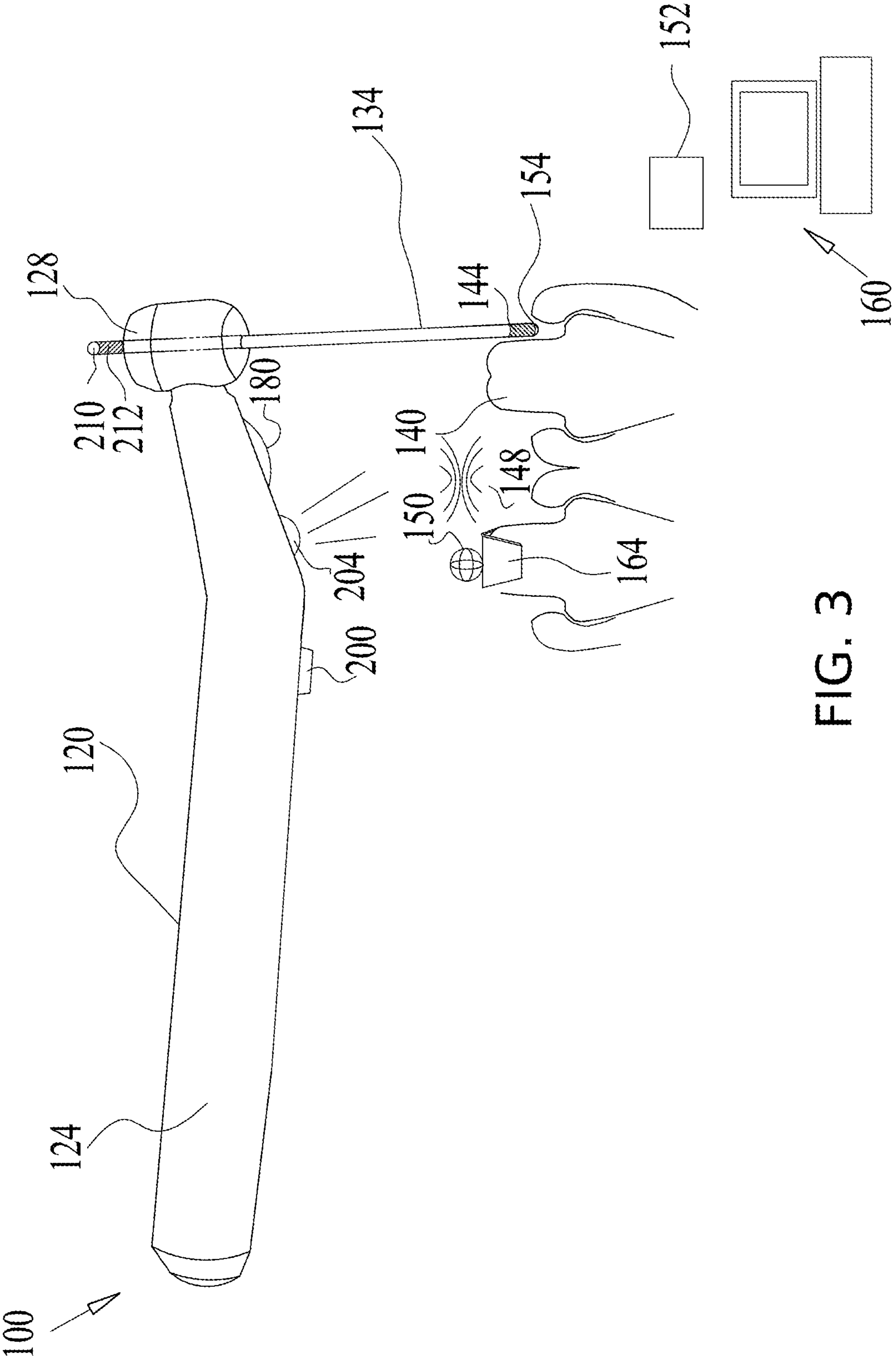
FIG. 3 is a simplified schematic illustration of a dental digital impression system comprising a water jet source, according to some embodiments of the present disclosure.

Methods of achieving and/or maintaining calibration between relative, electromagnetically determined positions and absolute position within the oral geometry are discussed, for example, in relation to block 904 of FIG. 1C, FIGS. 2A-2B and/or FIG. 3.

The tracked measurements are typically stored in a memory and can be used as input for accurately constructing portions of crowns, implants, bridges, prosthesis, and/or dentures for dental restoration or veneers or any other dental treatment which are to be fitted to the tooth in the region which the bur has been used to map. In some embodiments the volume of a prepared tooth 140 is obtained by "subtracting" from an initial volume all the volumes which were occupied by burr 134 during preparation. In some embodiments, positions received include positions at which the bur 134 is not in contact with a contour of tooth 140 itself. Optionally, the contour is generally defined as extending between the set of positions which are closest to some boundary of a position measurement set (e.g., the boundary closest to the tooth contour). Optionally, this definition is subject to refinement, for example, application of a statistical or other criterion to exclude artefactual position measurements.

In FIGS. 1A and 1B, the magnet 144 is shown placed at a proximal-to-the-tooth end of the bur, at or near a bur tip 154, which is configured to be positioned proximal to tooth 140. However, the magnet is optionally positioned at an opposite side, distal to the tooth 140; for example, at a protruding bur end 210 of FIG. 3.

The sensor 150 may be shaped in any suitable manner and may be placed at any suitable location. For example, the sensor 150 may be fixed to a neighboring tooth by a clip 164, by screws, by an adjustable band, by adhesive and/or by a plate produced in any suitable manner.

An example of adhesive is a bonding material, such as Bisco One-Step®, which provides a stable placement of sensor 150, while still being removable, for example, by peeling off at the end of the procedure.

In some embodiments, positioning of sensor 150 and magnet 144 is swapped. In the swapped configuration, magnet 144 acts as a beacon, placed at any other another suitable location within the mouth or oral cavity, for example, attached to one of the neighboring teeth. Sensor 150 is attached to the drill 120 or bur 134 to measure the relative 3-D spatial location (e.g. the distance and/or angle) of the bur 134 with respect to the beacon magnet 144. In some embodiments, the contour of the tooth 140 is measured according to the movements of the sensor 150 on bur 134 relative to beacon magnet 144.

In some embodiments, the bur 134 is formed with the magnet 144 integrated therein, as seen, for example, in FIG. 1A. Optionally, the magnet is integrated with the bur, for example by soldering to the bur rod. In some embodiments, the magnet is added as an extension of the bur rod. For example, a stainless steel bur rod is soldered or otherwise attached end-to-end with a rod of a magnetized ferromagnetic material. Optionally, the rod assembly is coated by abrasive powder, such as diamond powder, to produce a bur. In some embodiments the whole rod is made a magnetized ferromagnetic material, coated with abrasive powder. Optionally, the whole rod is made a ferromagnetic material, coated with abrasive powder, magnetized only at tip 144. Optionally, the whole rod is made a ferromagnetic material, coated with abrasive powder, and magnetized at a plurality of locations.

In some embodiments, a bur rod with at least a portion magnetized is not coated with abrasive powder. Optionally, such a nonabrasive bur is used for tracking along an oral contour without affecting the teeth or gums. Optionally, a nonabrasive bur is used for scanning the finish line 108 and/or the tooth portion below finish line 108 (shown by line 116), with the potential advantage that the tooth itself is unaffected. Optionally, the dentist can change to the non-abrasive bur after finishing all preparation, using it to mechanically scan all around finish line 108, and/or with some scanning of the region between finish line 108 and line 116 below the finish line. Potentially, this allows obtaining an accurate scan of finish line 108 and/or the tooth emergence angle. Optionally, the magnet 144 is formed as an attachment to the bur 134, such as a ring 158, as seen in FIG. 1B.

In some embodiments, other suitable means for creating a modulated electromagnetic field 148 of known geometry, and known electromagnetic flux are used, such as, for instance, one to three concentric orthogonal coils.

Reference is now made to FIG. 1C, which is a schematic flowchart of a method of tracking the position of a drill bur 134, according to some exemplary embodiments of the present disclosure.

At block 902, in some embodiments, the flowchart begins, and at least one remotely sensible position reference device is orally affixed in the mouth. The position reference device is optionally a sensor and/or a beacon. In some embodiments, the reference element comprises an electromagnetic field sensor 150, configured to detect one or more magnetic fields generated from the drill and/or the bur directly. In some embodiments, the reference element comprises a magnetic beacon; for example, magnet 144, for use in a configuration such as the swapped configuration described in relation to FIGS. 1A and 1B.

At block 904, in some embodiments, the position reference device is optionally registered to the current oral geometry of the mouth. In some embodiments, registration is direct.

Optionally, block 904 is skipped over. For example, by tracking bur volume location, the prepared surface can be obtained by summing all said volumes during preparation into a single volume. Then the surface of the summed volume close to the prepared tooth defines the new tooth surface, and can be used, for example, in crown preparation. In some embodiments, the finish line location can be added, e.g., by extending from this anchor surface. In some embodiments, matching of relative device movements to particular positions with respect to oral geometry is performed during and/or after preparation of a dental surface.

In some embodiments, the position reference device is directly imaged by an oral scanner, and incorporated into a 3-D model of oral structures of the mouth. In some embodiments, registration is indirect. For example, an intraoral scan of the prepared tooth/teeth and/or neighboring teeth to the sides and or in another jaw is taken before or after preparation and then an algorithm (for example, as described in relation to FIGS. 9-11) is used for alignment of 3-D models obtained from the IOS and the drill. Additionally or alternatively, a 3-D model is obtained by conventional impression of the relevant teeth. A potential advantage of a hybrid impression is to allow prepared tooth/teeth to be measured at high accuracy (e.g., within 30-150 μm), while the neighboring teeth are measured with potentially lower accuracy (but perhaps faster), as can be provided by some methods of IOS or direct impression taking. In another example, one or more fiducial marks (with which the position reference device is in a determined position relationship) are imaged in situ, and the position of the position reference device is inferred.

In some embodiments, positioning is determined by relative referencing. For example, the drill bur is placed at one or more locations in the mouth, while one or more corresponding readouts providing a current relative position of the drill bur and the position reference device are obtained. Optionally, the drill bur is placed at a position which is specified (e.g., along the gingival margin). Optionally, position is determined by an auxiliary optical scan. Optical calibration of bur tip position is also discussed, for example, in relation to FIG. 11A.

In some embodiments, movements of the drill bur along a tooth contour (optionally, movement without removal of material) are correlated with known contours of the teeth in order to precisely determine the mapping between a particular position output from the drill/position reference device pair and the actual geometry of the mouth. A potential advantage of this method is that it optionally does not require precise optical mapping of the position of either the bur or the position reference device within the mouth. An example of such a method is described, for example, in relation to FIGS. 10A-10D.

In some embodiments, several drill bur positions are recorded before the system accurately determines a correct position calibration (for example, by matching a traversed contour to a previously scanned contour). In this case, registration to the oral geometry optionally occurs one or more times during the loop of operations comprising block 906, 908, 910, and/or 912.

In some embodiments of the invention, calibration of position comprises accounting for a plurality of degrees of freedom in the setup phase. In some embodiments, the system tracks a distal cutting region of bur 134 (for example, bur tip 154). Optionally, bur tip 154 is modeled as a cylindrical region, an ellipsoid, a frustum, a cylindrical region and/or frustum with a rounded tip, or as another shape; for example (taking the example of a cylindrical region) by parameters of radius rt and height ht. In some embodiments, these parameters are variable, e.g., subject to wear on bur tip 154. Apparatus and methods for determining and/or re-calibrating modeling of bur tip 154 are described, for example, in relation to FIGS. 2A-2B. The effect of bur tip angle on contact position is also discussed, for example, in relation to FIGS. 9A-9C herein.

Knowing the surface geometry of bur tip 154 allows specification of the positions of a surface of bur tip 154 relative to the oral geometry when associated with translational coordinates specified, e.g., by $(x_t, y_t, z_t)$, and/or angular rotation coordinates specified, e.g., by $(\varphi_t, \theta_t)$.

In some embodiments, calibration of the system to allow determination of these coordinates optionally includes determining information about the position of one or more sensors relative to the oral geometry. For example, degrees of freedom affecting sensor 150 optionally include translational degrees of freedom (e.g.: $x_s$, $y_s$, $z_s$), and rotational degrees of freedom (e.g.: an azimuth $\varphi_s$, and an angular altitude $\theta_s$; there may also be a third rotational degree of freedom for axial rotation) relative to the oral geometry to which it is affixed. However, in some embodiments, calibration is relative—for example; calibration optionally comprises exact correspondence between a few optically scanned positions of the bur tip and corresponding electromagnetic position sensing readings, without a requirement to know absolutely where the sensor itself sits relative to the oral geometry.

In some embodiments, one or more offsets or angular adjustments are applied to sensed data in order to determine the position of the bur tip (including its surface) itself. For example, magnet 144 is optionally offset by a distance $d_{m,t}$ along an axis of the bur relative to the bur tip 154. This offset is optionally taken account of during calibration and/or dynamic position measurement. In some embodiments, there is potential ambiguity in the magnetic sensing data between two different relative translational positions of magnet 144 and sensor 154 (e.g., two different possible values of $(\delta x_{s,m}, \delta y_{s,m}, \delta z_{s,m})$), when relative orientation $(\delta\varphi_{s,m}, \delta\theta_{s,m})$ can also be changed. Optionally, an orientation sensor 231 is built into drill handpiece 124 to allow resolving this potential ambiguity. However, there can also be angular offsets generated between handpiece 124 and bur 134, e.g., due to lateral forces exerted on bur tip 154 during drilling. In some embodiments, one or more load sensors (or another method of encoding angular deflection) are provided with drill head 128, for example as described for load sensor 230 in relation to FIG. 5. In some embodiments, inputs from these additional measurement sources are also calibrated as part of block 904. For some sensors, calibration (e.g., of load sensors 230) is relatively stable between uses, so that re-calibration needs to be performed only occasionally. Optionally, calibration is done once during manufacturing.

In some embodiments, some measurement sources provide mutually redundant information. For example, load sensor and an imager optionally both measure angular offsets, though potentially for different conditions and/or with different accuracies. Such sensors are optionally calibrated to one another, for instance, at steady state, such that information from both measurements is in agreement.

At block 906, in some embodiments, movement of the drill bur, optionally including movement comprising tooth material removal is performed.

At block 908, in some embodiments, a 3-D model of oral geometry is optionally created and/or updated as the bur moves. Optionally, positions are recorded, and the 3-D model of oral geometry is updated off-line based on recorded positions. However, it is a potential advantage to update 3-D geometry as the drill moves, for example, to allow providing feedback (e.g., by showing the updated model) according to the progress of tooth preparation with respect to a tooth preparation plan.

In some embodiments, updating comprises subtracting a bur volume from a currently modeled tooth volume. Optionally, for example, if the tooth volume is not known before preparation starts, the starting volume is seeded with a block or other approximate volume sized and positioned to represent the tooth volume. Optionally, during preparation which reduces the tooth volume, the volume of the tracked bur is subtracted from the tooth volume wherever it intrudes, to obtain the contour of the prepared tooth surface.

Optionally, position data acquired before position calibration is determined (for example as described in relation to block 904) are retrospectively fitted to the 3-D model once position calibration is obtained.

Two types of 3-D model update in particular are noted. In one update type, the volume of a drill portion is moved across a previously mapped boundary of tooth material and into the position of the tooth material itself. This happens, for example, as the drill removes dental material. In some embodiments, the 3-D model of oral geometry is updated to reflect that such removal has occurred.

Additionally or alternatively, in some embodiments, the bur reaches to a point along a tooth contour which was previously unmapped. It could be unmapped, for example, because the contour was obscured from optical scanning by a layer of overlying gingival tissue. In some embodiments, a 3-D model of oral geometry is extended to show the shape of the tooth in areas which movement of the bur probes. Map extension is also shown and discussed, for example, in relation to FIG. 10D.

Movement of the bur into the volume of a tooth is blocked until the tooth material is removed. However, the bur will often occupy positions away from the contour of the tooth, e.g., as it is brought near to the tooth, and/or as it is moved from position to position during drilling. In some embodiments, all positions of the drill are recorded as part of a "point cloud" or "bur volume cloud". The point cloud is optionally analyzed for tooth contours, for example, by detection of boundaries up to which the bur often goes without passing, and/or at which movement of the bur slows (e.g., slows to the rate of material removal). Optionally, the union of the volumes which the bur volume occupies forms a complementary volume to the volume of the tooth which delineates its contours. In some embodiments, contour contact is determined by one or more additional methods. For example, deflection of the bur is optionally detected. A drill configured for the detection of bur deflection is described herein, for example, in relation to FIG. 5. Other detection methods include, for example, optical detection of contact and/or position (e.g., as described in relation to FIG. 4), detected slowing of bur rotation, detected change in electrical contact between bur and tooth, detected change in amplitude or frequency of drill vibrations, impulse applied upon the bur, and/or another method of contact detection. Optionally, an indirect measure of slowed bur rotation is used, for example, fluctuations in bur motor power, frequency, and/or temperature.

In some embodiments, another factor in determining tooth contour position is determining which portion of bur tip 154 is in closest proximity to the tooth contour. This can be, for example, substantially a contact line along a longitudinal extent of the bur when the bur is positioned substantially parallel and tangent to the tooth surface. When the tooth surface is concave, the contact can even be along a patch. When the bur tip is angled relative to the tooth surface, contact potentially transfers to concentrate at a more distal or more proximal region of the bur tip. In some embodiments, prior knowledge of a portion of the oral geometry is used in determining where tip contact is occurring, based on local angles of tooth geometry and a determined angle of the position of bur tip 154. In some embodiments, changes in tooth geometry angle over time (due to drilling) are taken account of in are part of this determination.

In some embodiments, contact position determination is further refined by taking into account the relationship between drill and/or cutting speed and load sensing. For example, a large load concentrating force on a relatively small corner of a tooth potentially results in a higher rate of cutting, and/or a different reduction in drill speed than a correspondingly large load spreading force over a larger surface area.

Optionally, material evaluation from the optical image, taken online and/or previously is incorporated into contact position determination. For example, different materials with different colorimetric properties have potentially different rigidities or other tendency for displacement under force, so that intrusion of a bur volume into a space may represent (at least initially) displacement rather than removal of material. In some embodiments, a processor tracking changes in dental geometry jointly takes into account a tendency of material to flex away from a drill bit as well as a rate at which a bur tends to erode that material, in order to estimate a resultant change in fixed geometry.

At block 910, in some embodiments, one or more actions based on current drill position and/or drill position history are performed At block 912, in some embodiments, a determination is made as to whether or not the procedure is continuing. If so, the flowchart continues, for example, at block 906. Otherwise the flowchart ends.

Additionally or alternatively to using the updated 3-D model during tooth preparation, the updated 3-D model is optionally used as a template for the manufacture of artificial structures which need to be fitted to existing dental geometry.

Reference is now made to FIGS. 2A and 2B, which are simplified schematic illustrations of a dental digital impression system 100 comprising magnetic and optical position sensing, according to some embodiments of the present disclosure.

In some embodiments, the dental digital impression system 100 comprises a camera 180 or any other suitable means for optical tracking. The camera 180 may be placed at any suitable location allowing view of a positioning target (such as landmark features of bur 134). For example, camera 180 is placed along the hand piece 124 of the drill 120. Further methods and systems for optical tracking are disclosed in the applicant's International Patent Publication No. WO2014102779, the contents of which are incorporated by reference herein in its entirety.

In some embodiments, camera 180 comprises a single optical aperture for 2-D imaging. In some embodiments camera 180 comprises a color camera, the color being used, in some embodiments, to distinguish between material types, for example, between teeth and gums. In some embodiments, camera 180 includes a plurality of optical apertures, and/or at least 2 synchronized cameras, for obtaining (e.g., stereoscopically) 3-D information about intraoral features and/or bur 134. In some embodiments camera 180 comprises a 3-D camera, for instance by use in conjunction with the projection of a structured light pattern. Combined optical tracking and electromagnetic tracking may be utilized for accurate 3-D tracking and measuring of the tooth 140, for example, as described in the following non-limiting examples.

Typically, dental drilling is performed by use of a bur 134 comprising a bottom portion, coated with a layer of an abrasive material 184 in a position where it can be brought proximal to the tooth 140. Abrasive material 184 (or another marker along bur 134) is optionally used as an optical marker for determining bur position. In some embodiments, determination of bur position includes taking into account an overall shape of the bur tip 154 (for example, as described in relation to FIGS. 1C and/or FIGS. 9A-9C). Optionally, the overall shape of the bur (optionally, of the bur tip or another portion of the bur) is used to define a volume which is subtracted from the tooth model, for example as described hereinabove, and/or which is summed over measured positions to define a complementary tooth volume, surface, and/or contour. Optionally, optical observation is used in the determination of this overall shape. Optionally, the profile of the bur tip 154 as viewed from one angle (for example, as the bur tip 154 rotates) is used to construct a model of the whole bur tip 154. For example, it is optionally assumed that the rotating bur tip 154 describes a rotationally symmetric volume of rotation.

Additionally or alternatively, in some embodiments, during a single drilling session, or following a number of drilling sessions, the abrasive layer 184 or other marking may erode and recede at locations along the bur 134. This potentially leads to calibration loss for the magnetic position sensing; e.g., since as the bur becomes slightly thinner at worn portions, the magnet may be allowed to come closer to the tooth than previously. In some embodiments, erosion of the abrasive layer is determined from the camera, and the change used to update the volume used for determining oral geometry. Optionally, use of combined optical and electromagnetic tracking identifies the receded locations of the abrasive layer 184, for example, by identifying the degree of thinning, and/or by identifying a mismatch between magnetically and optically detected positions, and recalibrating to compensate.

In some embodiments, tracking system 100 is configured to consider the receded location of the surface of eroded abrasive layer 184 and accordingly correct the tracked measurement of the bur magnet location relative to the contour of the tooth 140. Thus, the accuracy of resultant measurement of the tooth is maintained, although the positioning of the central axis of the bur 134 relative to the tooth 140 was altered during drilling. Optionally or additionally, the tracking system 100 is configured to provide an alert to the user or dental practitioner to replenish the abrasive layer 184.

In some embodiments, optical and electromagnetic tracking are coordinated for accurately identifying the portions of the tooth, such as the finishing line 108 relative to the contour of the tooth 140 and relative to its surrounding gingiva 102 such as by imaging a front view of the tooth 140, as seen in FIG. 2A, as well as a top view, as seen in FIG. 2B. This is a potential advantage during dental restoration or any other dental treatment for localizing the level of tracked contours to identified portions of the tooth, such as described in reference to teeth 104 and 110 of FIG. 1A.

Additionally or alternatively, in some embodiments, electromagnetic tracking is potentially distorted, for example, due to the presence of metallic or ferromagnetic objects in the oral cavity, such as dental fillings 190. Optionally, optical tracking is used to calibrate or compensate for this electromagnetic field distortion. For example, tooth measurements are calculated from an image provided by optical tracking of at least one tooth or other object in the oral cavity, optionally an object inserted and designated for this purpose. The magnetically tracked measurement of the relationship between drill handle and tooth 140 is then optionally calibrated according to the image. In some embodiments, optical tracking compensates or calibrates for electromagnetic field distortion by using tooth measurements calculated from an image provided by optical tracking of a visible portion of bur tip 154 to accordingly correct the bur tip 154 location relative to drill handle and/or tooth 140. Optionally, electromagnetic tracking provides the bur location when optical visibility is blocked.

Optionally, ambient magnetic field calibration is performed, for example, by occasionally and/or periodically (e.g. at the beginning and/or end of scan, and or when detecting a distorting trend in the magnetic field form) removing and/or turning off a generated tracking magnetic field and evaluating the ambient magnetic field which remains. Optionally, an additional electromagnetic excitation and/or pattern evaluation is used for characterization of external interference.

In some embodiments, the optical tracking is used for tracking the erosion or shortening of the bur 134. Optionally, the optical tracking is facilitated by tracking a marker, such as a ring or other object placed on the bur 134 or other suitable location. In some embodiments, registration of magnetic position information to absolution position within the oral geometry comprises correlation of optical tracking information with magnetic information. For example, optical readings are used to establish a current position within a previously optically determined 3-D model of oral geometry. The magnetic position reading at the current position is mapped to that position. Optionally, this is repeated for one or more additional positions, and a calibration of magnetically sensed position to geometrical position is interpolated between and/or extrapolated from associations made for these calibration points.

In some embodiments, a camera 180 is provided for use with a common dental turbine and/or other dental tool as an add-on to support bur tracking (for example, strapped or otherwise attached at a position such as the position shown for camera 180 in FIG. 2A). In some embodiments, said add-on is mechanically attached to said turbine handle and connected to tracking processing unit either with wires or wirelessly.

Reference is now made to FIG. 3, which is a simplified schematic illustration of a dental digital impression system 100 comprising a water jet source 204, according to some embodiments of the present disclosure. Optionally, drill 120 comprises a light source 200, such as a LED. Optionally, drill 120 comprises a water jet source 204 configured to spray the oral cavity with water during drilling for cooling the prepared tooth and/or bur 134. Potentially, the water jet obscures the dental digital impression, for example, by interfering with optical imaging by camera 180, and/or by deforming the electromagnetic field 148. In some embodiments, the water jet can be pulsed, such that between water pulses, a clear image of at least one tooth or any other object in the oral cavity and/or the drill bur 134 can be obtained by the camera 180 for optical tracking of the bur tip 154. Optionally, the images are captured using triggered signals synchronized with the water pulses to allow imaging in between pulses. Optionally, illumination from LED 200 is also synchronized to illuminate between water pulses.

In some embodiments, bur 134 is formed to protrude from a side of the head portion 128 distal from the tooth 140, forming a protruding bur end 210. Optionally magnet 144, or an additional magnet, is placed at bur distal end 210, away from the water jet. In some embodiment, deflection of the bur location due to water jet pulses is sensed. Optionally, the sensed deflection is compensated by the processing unit.

In some embodiments, for example as shown in FIG. 3, magnet 144 is proximal to the tooth-proximal end of the bur at bur tip 154. Optionally, bur 134 is formed with a mark or fiducial 212 at tooth-distal bur end 210. The mark 212, which is placed away from the water jet, is optionally tracked during dental digital impression (optionally by any suitable method such as optically and/or electromagnetically). In some embodiments, the location of tooth-proximal end 154 in contact with the tooth contour is calibrated relative to the location of bur distal end 210. Accordingly, the processor 160 may translate the tracked location at bur edge 210 combined with the location of head portion 128 relative to at least one tooth or other object in the oral cavity, to calculate the location of the proximal edge 154 for obtaining the accurate measurement of the tooth 140. Optionally, a tracked magnetic and/or optical region of a bur is positioned in a portion of the bur near the drill head. Optionally, locating the markers will allow non-linear extrapolation of the bur's tip according to a distance leading to the marker.

In some embodiments, magnet 144 is located on another portion of bur 134, and/or within the drill head portion 128; for example, coupled to the drill chuck. In some embodiments only optical markers or fiducials on the bur are used for locating bur 134 relative to head portion 128. In some embodiments, said markers are positioned on lower part of bur, at a position visible to camera 180 near the tooth. Optionally or alternatively, said markers are positioned over a distal part of bur 134, below head portion 128, such that they will not be blocked by water jet. In some embodiments, said markers can be marked over opposite side of bur 134, as shown at bur distal end 210 of FIG. 3.

Figure 4:
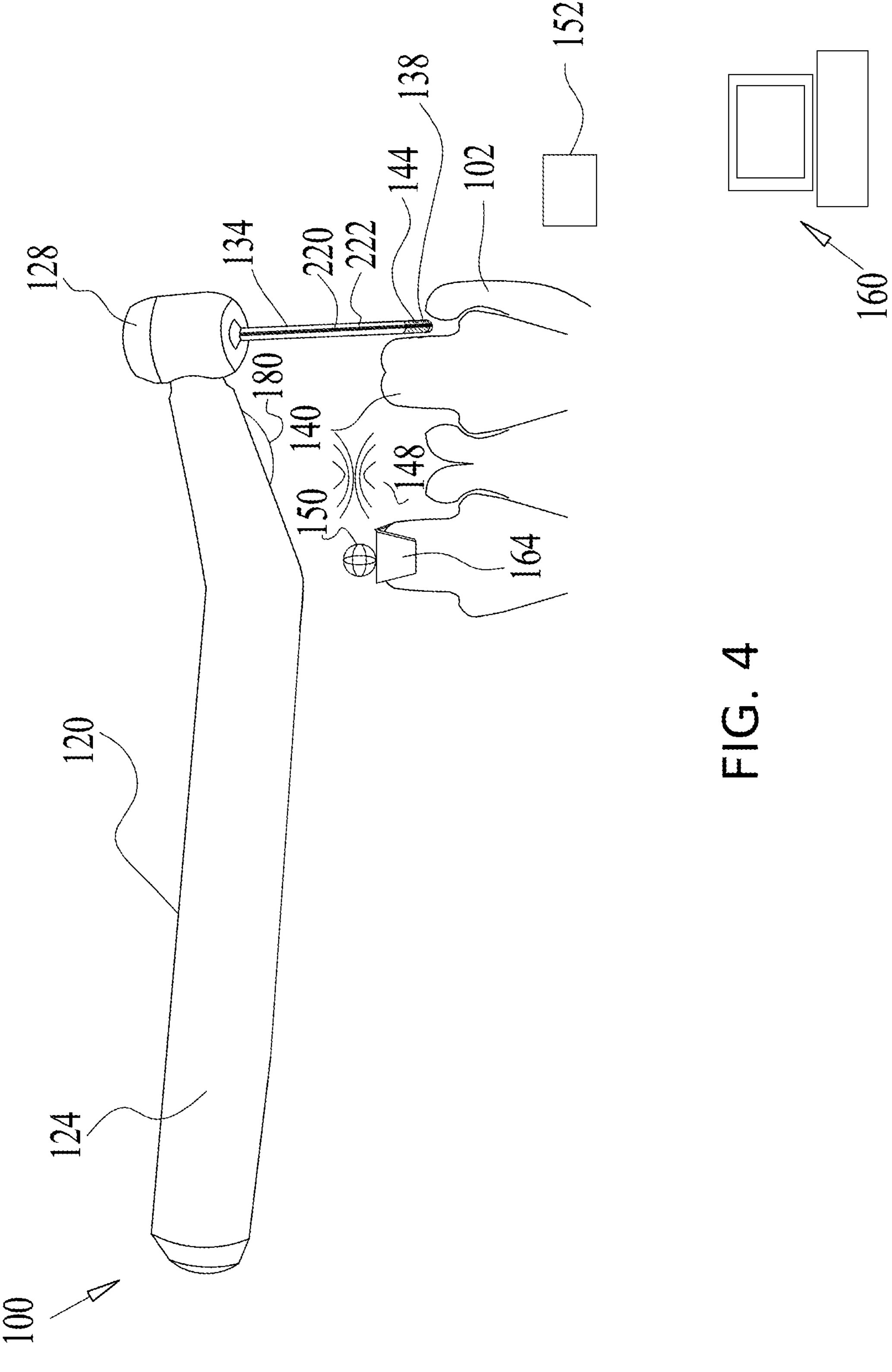
FIG. 4 is a simplified schematic illustration of a dental digital impression system comprising an optical fiber, according to some embodiments of the present disclosure.

Reference is now made to FIG. 4, which is a simplified schematic illustration of a dental digital impression system 100 comprising an optical fiber 220, according to some embodiments of the present disclosure. In some embodiments, optical tracking is performed by use of an optical fiber 220 inserted in a lumen 222 formed in the bur 134 or any other location (e.g., along a groove of the bur). Optionally, optical fiber 220 is used for chromatic imaging of the tooth 140 and its surroundings.

In some embodiments optical fiber 220 is used to measure tooth reflectance and/or spectral reflectance. Optionally, optical fiber 220 emits illumination of at least one wavelength. Optionally, optical fiber 220 measures light reflected back into optical fiber 220. Optionally, probe light is provided from another source, for example a LED or laser illuminating a region in the vicinity of an inlet to optical fiber 220.

Optionally, optical fiber 220 is used to distinguish between a proximate white surface, thereby identifying the tooth 140, and a pinkish surface, thereby detecting the surrounding gingiva 102. Optionally, relatively darker and lighter areas are detected. For example: during drilling, once the bur 134 passes the finishing line 108, the reflectance back to optical fiber 220 potentially reduces significantly, and/or the spectra changes from a white reflectance to a more pinkish one, thereby identifying nearby portions of the tooth 140 and/or portions of the oral cavity by chromatic variations. Optionally, optical property differences between another pair of materials is identified; for example, differences in light collected from enamel and dentin (e.g., due to differences in light scattering and/or color). In some embodiments a single fiber 220 is utilized. Optionally, a bundle of optical fibers or a single fiber with a plurality of cores is used. Optionally, chromatic imaging is used separately or in addition to the optical and/or electromagnetic tracking described in relation to FIGS. 1A-3.

In some embodiments, the plurality of optical fibers (e.g., bundles of optical fibers or cores) is further exploited for improving estimation of the contact point of the bur tip 154 with the tooth 140, to allow further modeling precision (e.g., a position of maximum light return is optionally identified with a position of contact). Optionally, the bundle of fibers or the cores is split, e.g., at the bur tip 154 and directed towards different points, for example, different contact areas along the length of the bur tip 154. Optionally, a fiber light inlet and/or outlet is at least partially radially directed from a bur 134, and one or more time-varying properties of sampled light are used in the measurement of a rotational angle position of the bur 134 as it rotates, and/or in measurement of a rate of rotation of the bur 134. The fiber or core point closest to the actual contact point of tip 154 can be evaluated through algorithmic processing of the outputs received from the separate fibers or cores.

Optionally, the additional information gained by the optical fiber(s) concerning the material located below the bur's head, is used for control of the system's operation, e.g., modification of the bur's speed, and/or water jet pulse operation variation.

Figure 5:
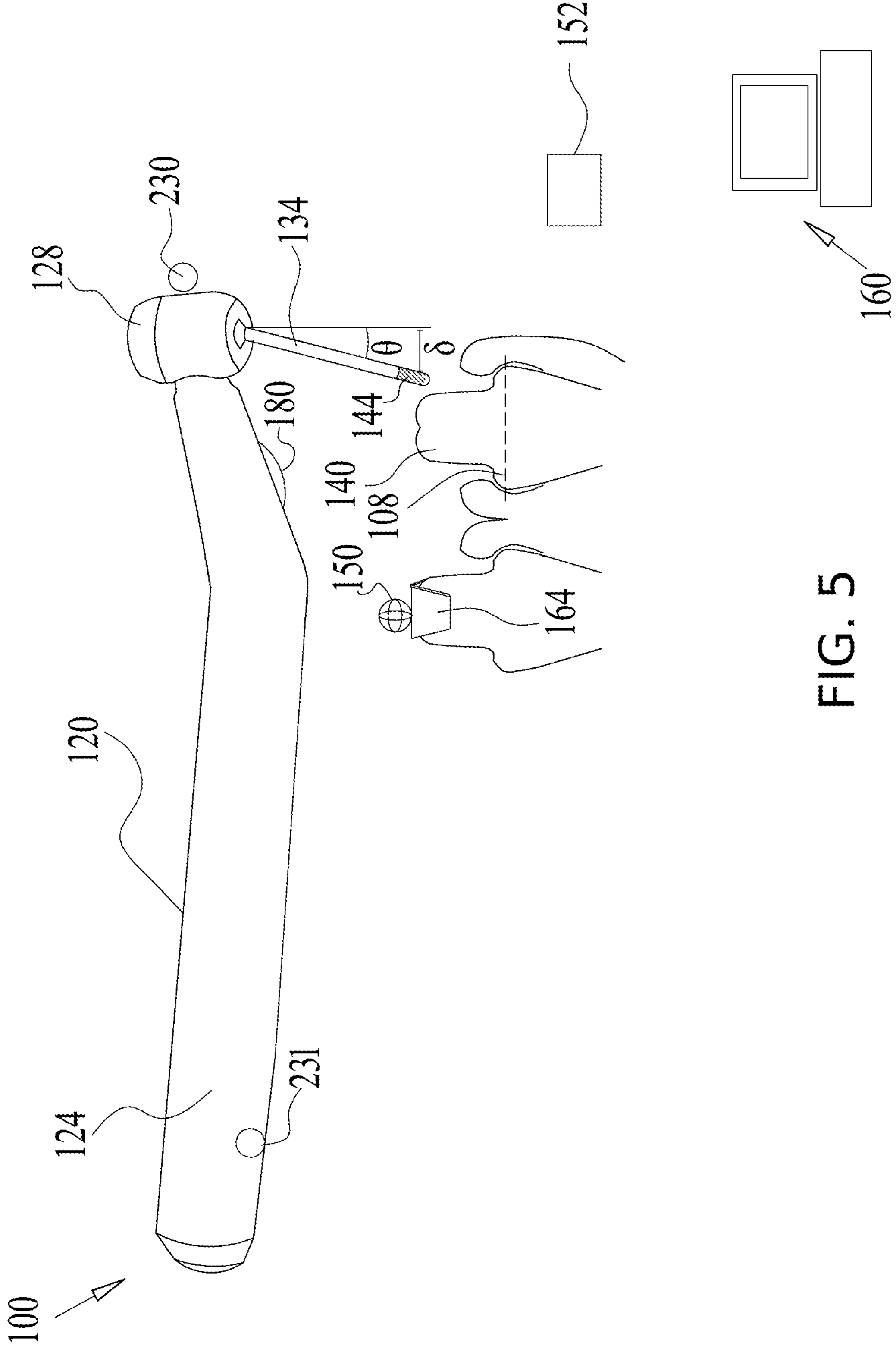
FIG. 5 is a simplified schematic illustration of a dental digital impression system configured for determination of a bur tip deflection, according to some embodiments of the present disclosure.

Reference is now made to FIG. 5, which is a simplified schematic illustration of a dental digital impression system 100 configured for determination of a bur tip deflection, according to some embodiments of the present disclosure. In some embodiments, optionally in conjunction with the optical and/or electromagnetic tracking, dental digital impression system 100 comprises a load sensor 230. Optionally, a load (for example, a lateral load) applied to the drill 120 during drilling is detected by a load measurement sensor 230. Load measurement sensor 230 is optionally in physical contact with the drill 120 or away therefrom. Optionally, the load applied by the user is measured at the handpiece 124 or the head portion 128 or any other suitable location. Assuming elastic connection of bur 134 to head portion 128, the linear deflection δ of the bur 134 and/or the angular deflection θ of the bur 134 relative to the head portion 128 is optionally considered to be proportional to the load F, e.g.:

$$F \propto \delta; F \propto \Theta$$

Optionally, load sensing is provided to allow determination of direction of deflection as well as magnitude. For example, two orthogonally sensing load sensors are provided.

Optionally, the angular and/or linear spatial location of the bur 134 is derived from detection of the load F. Processor 160 is optionally configured to process the measured load F during drilling, and accordingly to calculate the angular and/or linear spatial location of the bur 134, relative to drill head 128. Optionally, this is used with other position measurements, such as magnetic and/or optical position measurements of bur 134 in the measurement of a contour of tooth 140. For example, optical tracking is optionally used to track the movement of the drill 120, at any location thereof. Upon receiving the tracked movement of the drill 120 and the dynamically measured load, the processor 160 is optionally configured to process the measured load F and tracked drill movement during drilling (e.g., positions of headpiece 120 relative to at least one tooth or other object in the oral cavity), and accordingly calculate the angular and/or linear spatial location of the bur 134 as it follows the tooth contour, and from this derive measurement of tooth 140 itself.

As another example: in some embodiments, tip spatial location (x, y, z) is obtained from tracking magnet 144, and bur angle is obtained by combining information of bur angle relative to drill 120 and drill 120 angular information obtained from tilt/rotation sensor 231 embedded with drill 120. Such a sensor can be implemented for example, using a MEMS gyro, accelerometer and/or digital compass (optionally embedded into a single chip).

In some embodiments, a plurality of magnets 144 is provided upon bur 134; for example, one near drill head 128, and one near bur tip 154. Optionally, the arrangement is configured (for example, by relative inversion of the orientation of the magnet poles) so that the pattern of the resultant magnetic field received at the sensor 150 can be used to encode the angle of the bur. Position encoding is extracted, for example, based on pre-calibrated matched filtering, and/or another signal processing technique.

Optionally, use of more than one magnet allows the determination of bur location in more degrees of freedom (DOF) (x, y, z and 3 angles, for example), to obtain accurately the position of the bur volume (e.g. to allow subtraction from the tooth volume). In some embodiments more than one electromagnetic sensor (for example, sensors at relatively widely separated locations) is used for determining the additional DOF information.

Additionally or alternatively, optical tracking of plurality of optical markers and/or fiducials is used. The markers can be encoded through color, form, size etc. Optionally, the deviation of optically tracked markers from pre-calibrated location will encode the angle deviation of the bur.

In some embodiments, the drill load F is tracked and measured to indicate the location of the drill 120 relative to the tooth finishing line 108, e.g., to determine if the drill is in contact with the tooth contour. For example, drill 120 in contact with the tooth 140 receives a certain load, while drill 120 at a space intermediate to tooth 140 and the gingiva 120 (for example, after passing the finishing line 108) potentially receives a smaller load. This sensing is a potential advantage for determining whether a particular position measurement is of a tooth-contour contacting position, or of a position away from the tooth contour.

In some embodiments, data acquisition from the load sensor is indexed to the rotation of the drill bit. Optionally, load sensor data acquisition is performed at a frequency comparable to or higher than the rotational rate of the dental bur. Optionally, data acquisition is gated by the rotational position of the dental bur. Optionally, the timing data is used to distinguish angular offset information for the bur during different rotational phases. This is a potential advantage, for example, if the drill bit develops a slight wobble. For example, wobble in one direction is potentially constrained by contact with the oral geometry, while wobble in another direction is free. In some embodiments, phase information is used to distinguish which angular offset occurring during a drill bit rotation should be used in determining the local position of a tooth contour. Optionally, induction and/or suppression of wobble are used to indicate whether a bur is touching a tooth or not.

In some embodiments, the load sensor may operate in a separate system excluding the optical and/or electromagnetic tracking. In some embodiments load sensor information is used for providing a feedback to dentist if applied force is too high.

The accurate tooth measurement obtained by implementing the dental digital impression system 100 described in reference to FIGS. 1A-5, can be implemented in various systems and methods for dental restoration or any other dental treatment.

In some embodiments (optionally embodiments with or without load sensor 230), a handpiece orientation sensor 231 is provided. Optionally, this orientation sensor is a geomagnetic field sensor. It should be noted that magnet 144, though it may influence magnetic fields in the vicinity of orientation sensor 231, is optionally in a substantially constant position relationship to it so that changes in orientation relative to the local geomagnetic field can be isolated. Optionally, orientation sensor 231 is located spaced away from magnet 144 to reduce interfering effects. Optionally or alternatively, orientation sensor comprises an accelerometer.

Figure 6:
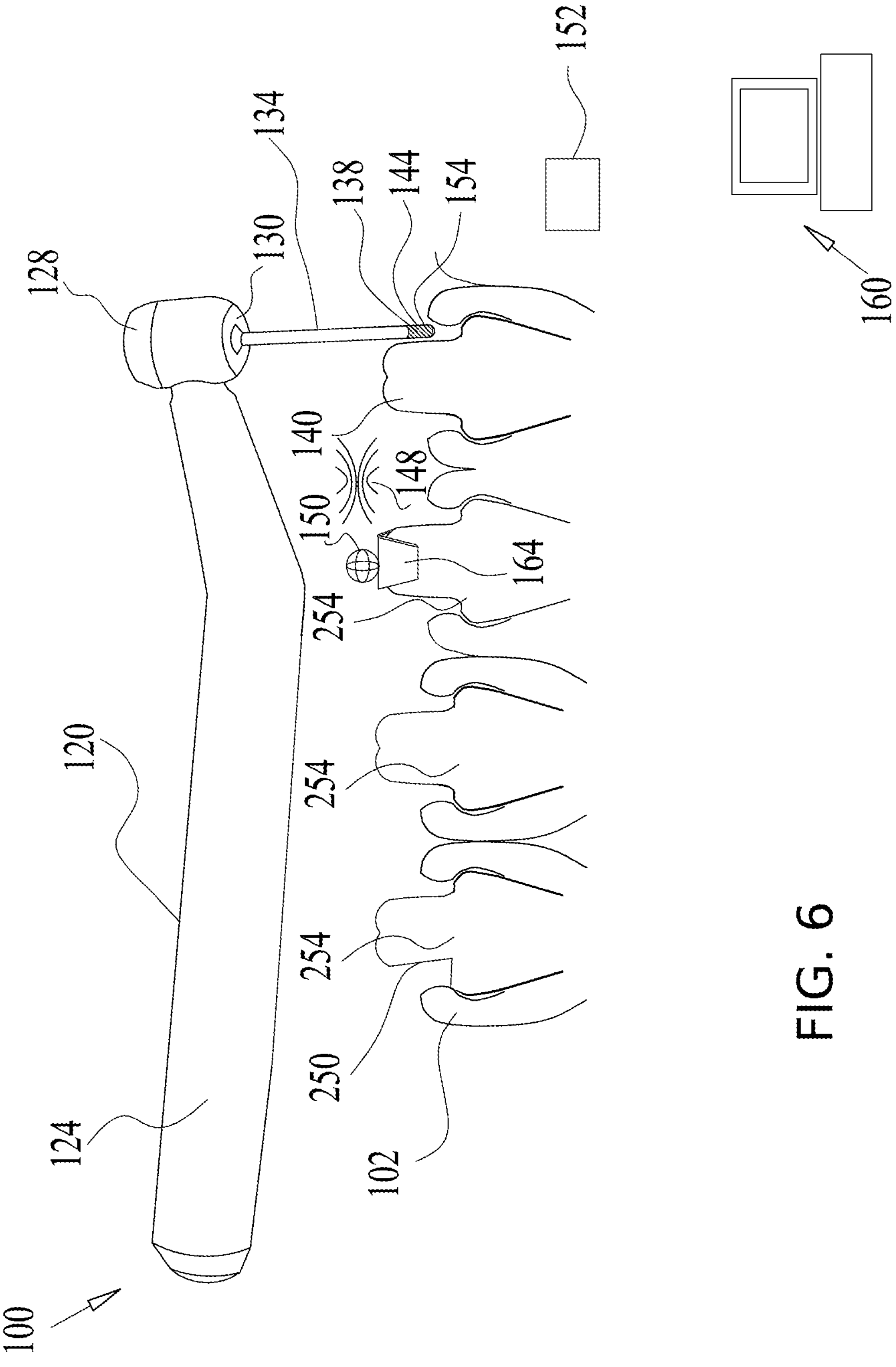
FIG. 6 is a simplified schematic illustration of a dental digital impression system configured for determination of a bur tip position, according to some embodiments of the present disclosure.
Figure 12:
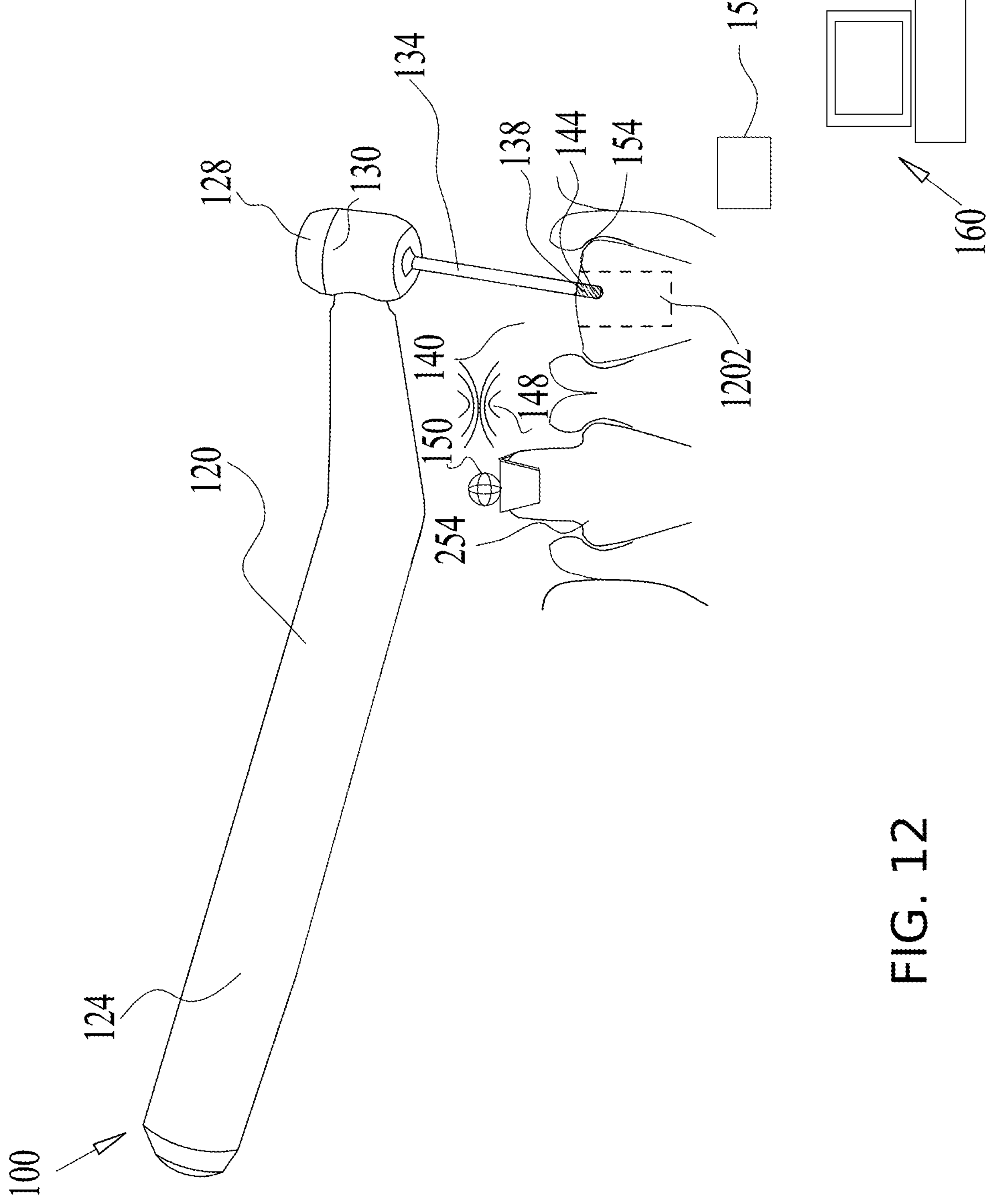
FIG. 12 is a simplified schematic illustration of dental digital impression system drilling a socket for receiving of a dental implant, according to some embodiments of the present disclosure.

Reference is now made to FIG. 6, which is a simplified schematic illustration of a dental digital impression system 100 configured for determination of a bur tip position, according to some embodiments of the present disclosure. Reference is also made to FIG. 12, which is a simplified schematic illustration of dental digital impression system 100 drilling a socket for receiving of a dental implant, according to some embodiments of the present disclosure.

As seen in FIG. 6, a natural tooth is optionally formed with a slope 250. In practice, mounting of a dental bridge or any construction used for a plurality of teeth 254, may be interfered with (e.g. distorted), by slope 250. Potentially this prevents the bridge from being properly mounted on the plurality of teeth. In some embodiments, dental digital impression system 100 offers a method for highly accurate measurement of a contour of a single or a plurality of teeth including measurement of the slope 250 as described in reference to FIGS. 1A-5. With knowledge of the measured shape of slope 250, the dental practitioner constructing the bridge optionally accounts for the slope 250, forming the bridge to appropriately fit the slope 250 and/or any other inclines or deformities of the teeth.

Optionally, prior to the initial drilling step, an image of the oral cavity is attained. The oral cavity image can be processed, for example, by a CAD/CAM program and used for planning required tooth preparation. For example, a planned volume of dental material (e.g. portions of the gingiva and/or tooth) is designated to be removed. This in turn is optionally used to specify required activity of the drill 120 during the drilling step. This tooth preparation plan can be used by the processor 160 which tracks the drill bur 134 (for example, as described herein) to control the bur operation. For example, when bur 134 is outside the planned volume of dental material to be removed, and/or as bur 134 nears a margin of a planned volume of material removal while it is actively removing material; the bur operation is optionally stopped or slowed down. Additionally or alternatively, the user is provided with a visual, audio and/or vibration indication when the bur 134 is outside (and/or reaching a margin of) the planned volume of dental material to be removed.

The visual indication can be, for instance, a red indicator on the drill handpiece 124. Additionally or alternatively, a visual indication is shown on a display; for example, a display of a dynamic image of the drill 120 and the prepared tooth, showing the spatial relationship between the drill 120 and the prepared tooth. The display is optionally as a 3-D image, and/or as an image comprising one or more sections, for instance. Optionally, a selected color used is used for indication of the planned volume of dental material to be removed.

A potential advantage of using bur tracking is an increase in the accuracy with which such a drilling plan can be tracked. Potentially, exploiting the accuracy of bur measurements obtained by use of dental digital impression system 100 enhances the accuracy with which specifications of the drilling plan can be followed. Optionally, accuracy of plan following is increased to a level where the plan itself is usable as a template for dental prosthetic preparation. Optionally, the plan allows prosthetic preparation (e.g., by on site 3-D printing and/or CNC machining) concurrent with or even before tooth preparation.

In some embodiments, once the CAD/CAM preparation management plan is made, the drilling is controlled by use of one or more guiding tracks that mechanically interface with drill 120; for example, by constraining the movement of guide track-interlocking guide pins located on drill 120. Optionally, the one or more guiding tracks are formed by 3-D printing and/or CNC machining of the guides. Optionally, the guides are manufactured as part of an adaptor configured to be attached to a neighboring tooth or plurality of teeth, and/or to other objects in the oral cavity. Optionally, the manufacturing is specified based on a 3-D scan of the oral cavity.

In some embodiments, the guiding adaptor is formed with guides (e.g., slots) for guiding designated guiding pins located on the drill 120 during the tooth preparation step. Optionally in use together with a guiding adaptor, the dental digital impression system 100 can be used to track the drill bur 134. Optionally, tracking information is used to compensate for the tolerances between the handle guiding pins and bur tip location. Optionally, in embodiments using an electromagnetic tracking system (e.g. such a system as described herein), the sensing coils 150 are located inside the 3-D printed tooth adaptor, and the rotating magnet 144 may be placed at bur tip 154. Optionally, a camera is located inside an adaptor, and oriented for optical tracking of bur location. Optionally, at least a portion of the adaptor is printed by a 3-D printer such that it fits at least one tooth in the oral cavity (for fixation and/or for specificity of positioning). Optionally, the adaptor incorporates and/or is configured to attach to a camera or electromagnetic sensor (additionally or alternatively, a magnet) for tracking the bur tip 154. The bur tracking complements adaptor guidance by providing a potentially more accurate 3-D model of the prepared tooth or teeth, for example, for production of a crown or bridge. The bur tracking information can be used, for instance, to control the drill operation as described herein, thereby increasing the accuracy of the activity of the drill 120 during the drilling step. Optionally, the ranges of movements allowed by the guide are used as constraints on the processing of electromagnetic and/or optical information to yield bur position data.

In some embodiments of the invention, preparation of an oral cavity comprises the formation of a socket 1202 (FIG. 12) in a jawbone; for example, in preparation for receiving a dental implant.

In some embodiments, a shape of socket 1202 is optionally at least partially defined during preparation of the socket itself. Optionally, tracking of the positions of the bur tip 154 allows the shape of the socket to be accurately determined, based, for example, on the volume tracked by the bur tip where it intrudes into the volume of the bone. In contrast to traditional pre-implantation preparation, where a bone socket is prepared according to the predefined dimensions of a selected implant, this potentially allows dimensions of the implant to be selected based on the dimensions of the socket prepared to receive it. The implant is optionally 3-D printed, or otherwise custom fabricated, according to a design which incorporates information about the actual size and shape of the socket. A potential advantage of this is to allow preparation to follow the actual geometry of the jawbone, which can help prevent over-drilling in socket diameter and/or length relative to the actually available bone substrate dimensions. In some embodiments, socket dimensions are planned out before preparation (e.g., based on known oral geometry), and position tracking is used during preparation to guide drilling so that the right socket shape is formed. In some embodiments, position tracking for determination of socket shape is performed during drilling itself. Additionally or alternatively, a socket shape is determined after drilling, for example, by using a probe (optionally, a non-bur probe) sized and shaped to map out the inner surfaces of the cavity.

Figure 7:
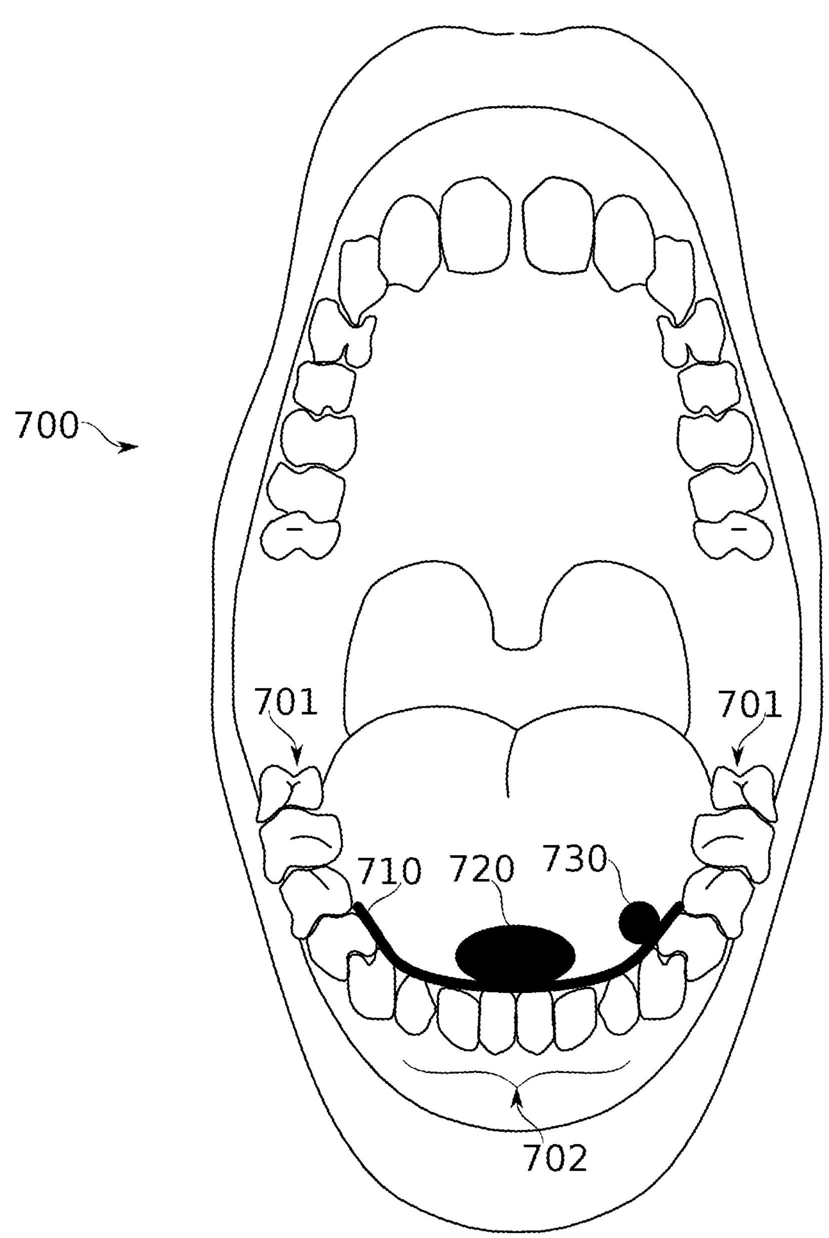
FIG. 7 schematically illustrates a marker fixation device comprising a magnetic sensor, for use in magnetic tracking of a dental instrument, according to some embodiments of the present disclosure.
Figure 8:
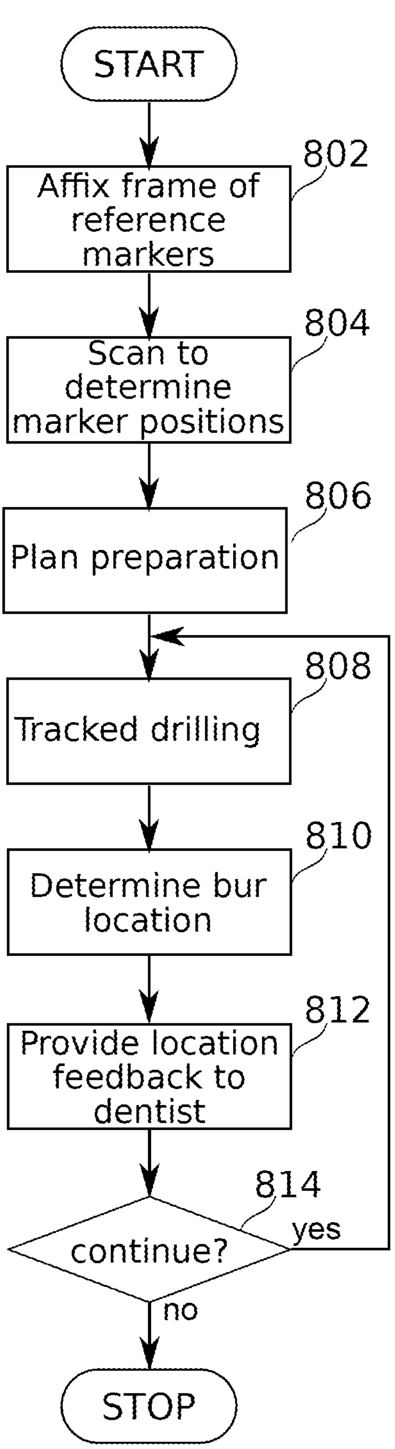
FIG. 8 is a schematic flowchart of a method for guided preparation of a tooth for receiving a veneer, according to some exemplary embodiments of the present disclosure.

Reference is now made to FIG. 7, which schematically illustrates a marker fixation device 710 comprising a magnetic sensor 720, for use in magnetic tracking of a dental instrument, according to some embodiments of the present disclosure. Reference is also made to FIG. 8, which is a schematic flowchart of a method for guided preparation of a tooth for receiving a veneer, according to some exemplary embodiments of the present disclosure.

In some embodiments, existing dental structure within mouth 700 (e.g., comprising teeth 701) is determined, for example by an optical scanning method. Guidance of a working (e.g., cutting or grinding) portion of a drill bur, in some embodiments, comprises measurement of the drill bur position relative to a magnetic sensor 720. Furthermore, in some embodiments, the position of the magnetic sensor 720 itself is determined relative to the scanned geometry of the mouth by its relationship to one or more fiducial marks 730, with respect to which the magnetic sensor is fixed, for example, by the superstructure of a marker fixation device 710.

In some embodiments, marker fixation device 710 is a clamp, comprising, e.g., an elastic mechanism which is at least partially secured by pressing outward against the dental structure to which it is affixed. In some embodiments, marker fixation device 710 is attached to the mouth 700 using flexible and high viscosity materials, such as putty elastomeric material. In some embodiments marker fixation device 710 is attached using bonding materials, such as Bisco One-Step®, and peeled off and the end of the procedure.

Optionally, marker fixation device 710 is used to establish a positioning frame of reference when preparing one or more teeth 701 to receive a dental veneer. A veneer is a layer of material placed over a tooth: for example, to modify the aesthetics (color and/or shape, for example) of a tooth and/or to protect the tooth's surface from damage. Optionally, a veneer is attached to one or more front teeth 702. Optionally, preparation of a tooth to receive veneer comprises removal of a portion of existing tooth structure.

In some embodiments marker fixation device 710 is designed from a scan of a portion of the palatal or lingual front side of the jaw. Optionally, marker fixation device 710 is constructed by 3-D printing of a customized 3-D clamp according to the design.

With reference now to the flowchart of FIG. 8: at block 802, in some embodiments, one or more markers 730 suitable for establishing an optical frame of reference within the mouth 700 are orally affixed. For example, marker fixation device 710 is affixed to teeth 701 of the mouth 700. Optionally, marker fixation device 710 is affixed to the inner (lingual) side of the teeth 701.

At block 804, in some embodiments, teeth 701 (e.g., teeth 702) to be prepared are scanned with an intraoral scanner, to localize the elements of marker fixation device 710 in 3-D relative to the existing dental structures of mouth 700. Optionally, the scan (and/or other position sensing data) also includes marker 730 and/or specifies its positional relationship to the teeth 701 to be prepared. In some embodiments, this allows the relationship of other elements of marker fixation device 710 (in particular, magnetic sensor 720) to be determined relative to the teeth 701 to be prepared as well. For example, in some embodiments, the distances among two or more markers 730 and magnetic sensor 720 are fixed. In some embodiments, magnetic sensor 720 is also used as a marker 730. In some embodiments, marker fixation device 710 is constrained to fit within an inner perimeter of a dental arch comprising teeth 701 and distances between elements attached to marker fixation device 710 along the perimeter are fixed, such that knowing the course of the perimeter (e.g., from an oral scan) and the positions of one or more of markers 730 also constrain the position of magnetic sensor 720.

Optionally, oral scans which locate marker fixation device 710 within the mouth are partial scans, which are registered to data from a more complete scan in order to determine the position of elements attached to marker fixation device 710.

At block 806, in some embodiments, a 3-D model derived based on the oral scans is used for planning the veneers and/or showing the planned result to the patient. Optionally, the plan is produced in form which is used as reference in one or more of the following steps 808, 810, and/or 812.

At block 808, in some embodiments, the dentist begins (or continues) use of a drill with high accuracy tracking (optionally, bur tracking; for example, magnetic bur tracking as described in relation to FIGS. 1A-6 herein) for accurately removing a thin layer from a portion the front side of the teeth; for example, according to a plan produced in the design phase of block 806. Optionally, burr location is tracked using magnetic sensor 720 attached to marker fixation device 710. In some embodiments, high accuracy comprises tracking of movement of the bur to an accuracy of 200 μm or less: for example, within the range of 30-100 μm or within the range of 30-200 μm.

At block 810, in some embodiments, a processing unit uses the known 3-D location of magnetic sensor 720 relative to the at least one marker 730 and the location of magnetic burr relatively to magnetic sensor 720 to accurately locate the bur relative to the scanned 3-D model.

At block 812, in some embodiments, the processing unit provides guidance to the dentist for the removal tooth layers according, for example, to the preparation design of block 806. In some embodiments, the guidance is provided by visual and/or audio feedback. In some embodiments, the drill is automatically slowed and/or stopped as it reaches a boundary of the tooth volume planned to be removed.

At block 814, in some embodiments, a determination is made as to whether or not the procedure is complete. Optionally, the dentist makes this determination based on an indication of completion of the planned tooth material removal from the processing unit. If the procedure is complete, the flowchart ends. Otherwise, the flowchart returns to block 808 for continued drilling.

Figure 9A:
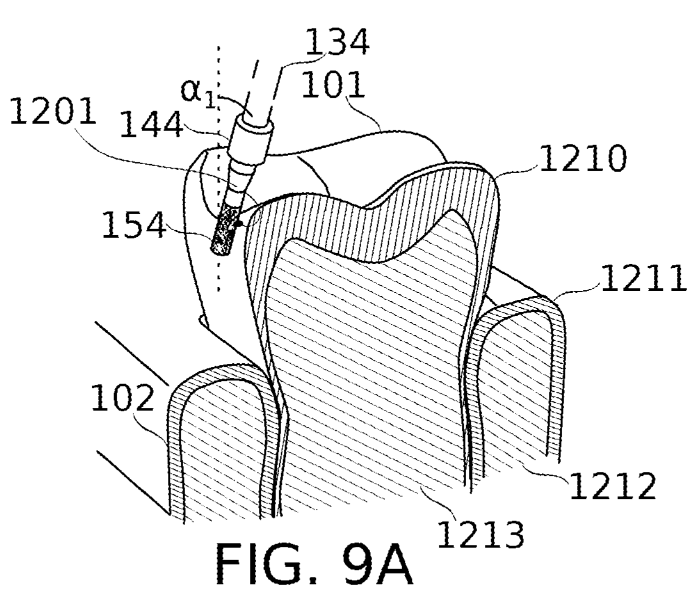
FIGS. 9A-9C schematically represent change in the contact position of a dental drill bur tip with a tooth as a function of angle, in accordance with some exemplary embodiments of the present disclosure.
Figure 9B:
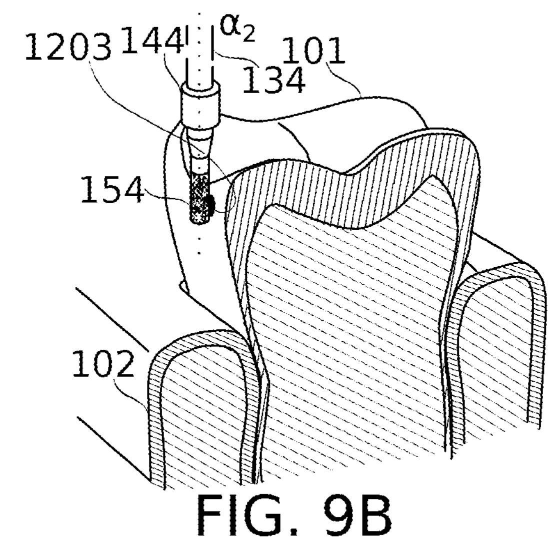
Figure 9C:
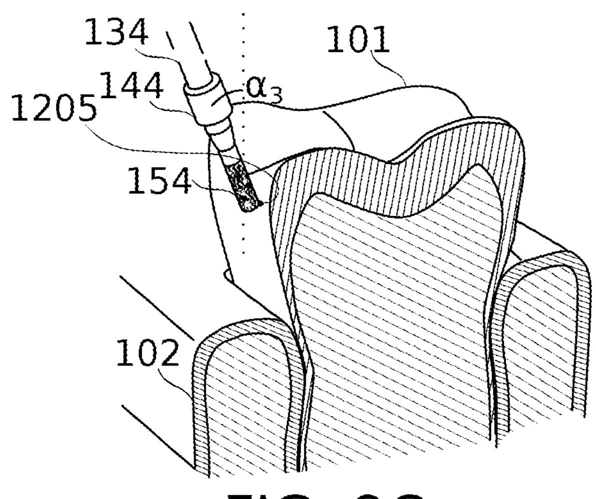

Reference is now made to FIGS. 9A-9C, which schematically represent change in the contact position 1201, 1203, 1205 of a dental drill bur tip 154 with a tooth 101, as a function of angle $\alpha_1$, $\alpha_2$, $\alpha_3$, in accordance with some exemplary embodiments of the present disclosure.

Optionally, a bur tip 154 is brought into contact with the surface of a tooth 101 within a range of angles (represented in the figures by angles $\alpha_1$, $\alpha_2$, and $\alpha_3$). In some embodiments of the invention, contact position-based mapping accuracy is increased by taking into account the potential for changes in bur angle to also change the location of contact 1201, 1203, 1205 with the tooth 101, relative to the position of a magnet 144 and/or sensor 150. Methods and devices for determining this angle are described, for example, in relation to FIGS. 1C and 5.

For example, in the bur 134 position of FIG. 9A, contact region 1201 is relatively toward the top (proximal portion) of bur tip 154 when oriented at angle $\alpha_1$. As the angle changes to angle $\alpha_2$, contact position 1203 moves toward the middle of the bur tip 154, while at angle $\alpha_3$, contact position 1205 is near the bottom (distal end) of the bur tip 154. In some embodiments, for example as described in relation to FIG. 1C, the geometry of bur tip 154, along with known and/or approximated details of the geometry of tooth 101 is taken into account in determining a contact position. This can be an iterative procedure, particularly as the bur reaches toward regions of the tooth geometry (for example, between tooth 101 and gingiva 102) for which a contour map has not yet been established. For example, it is optionally assumed that a tooth contour continuous into an unmapped territory at the same slope as an edge of the mapped zone. If an inconsistency with this assumption is noted (for example, by a closer approach of any portion of the bur surface than the provisional contour allows for), then the tooth model is updated accordingly. It should be noted that once a significant amount of drilling has been performed, it will be generally true that the deepest observed intrusions of the surface of bur tip 154 into the direction of tooth 101 will allow substantially continuous definition of the actual tooth contour.

For purposes of reference, it should be noted that FIGS. 9A-9C (as well as FIGS. 10A-10B) show tooth 101 and gingival tissue 102 in schematic cross section, revealing an example of distinctions in oral anatomy between gingival tissue 1211 itself and the underlying alveolar bone 1212; and between the enamel of the tooth 1210, and underlying tooth tissues 1213 including dentin and pulp.

Reference is now made to FIG. 10A, which schematically shows a mapped contour 1002 of a tooth 101, superimposed on the tooth 101, according to some embodiments of the present disclosure. Optionally, mapped contour 1002 is obtained by any means useful for taking a dental impression, for example an optical scan. Reference is also now made to FIG. 10B, which schematically shows a point cloud comprising drill bur position measurement points 1004, 1006 in proximity to a tooth 101, according to some embodiments of the present disclosure. Optionally, some of the position measurements 1004, 1006 comprise measurements made while the drill bur is located at least partially below the gum line; e.g., between gingiva 102 and tooth 101. Measurement locations 1004 (e.g., location 1004A), marked with small circles, represent locations where the drill bur is not in contact with tooth 101. Measurement locations 1006 (e.g., location 1006A), marked with larger circles, represent locations where the drill bur is in contact with tooth 101 (for simplicity, potential changes in tooth contour due to drilling are not indicated). Optionally, each marked location may be understood to indicate position(s) of closest approach of a bur tip surface to the actual or estimated position of the tooth contour.

Figures 11A, 11B:
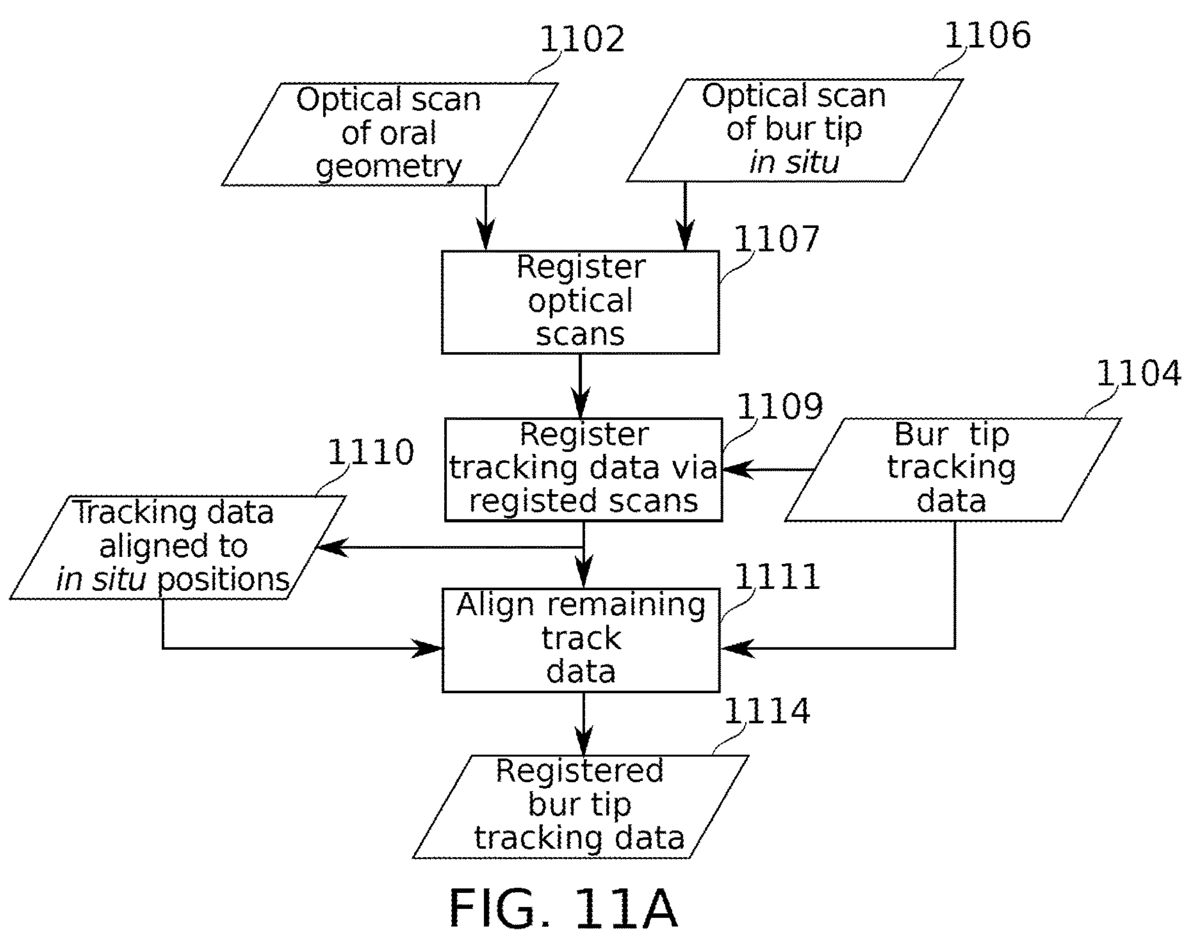
FIG. 11A is a flow chart schematically illustrating a method of optically calibrating the position of a bur tip in relation to an optical scan of oral geometry, according to some exemplary embodiments of the present disclosure.
FIG. 11B is a flow chart schematically illustrating a method of fit-calibrating the position of a bur tip in relation to an optical scan of oral geometry, according to some exemplary embodiments of the present disclosure.
Figure 11C:
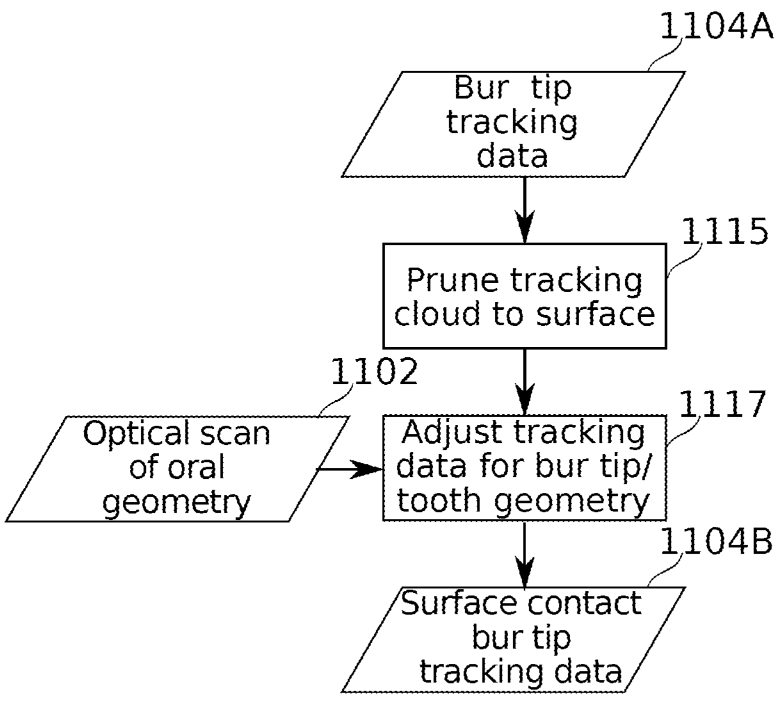
FIG. 11C is a flow chart schematically illustrating the conversion of bur tip position data to estimated tooth contour contact regions, according to some exemplary embodiments of the present disclosure.

Relating to operations described in relation to FIG. 10A, reference is now made to FIG. 11C, which is a flow chart schematically illustrating the conversion of bur tip position data to estimated tooth contour contact regions, according to some exemplary embodiments of the present disclosure. At block 1115, in some embodiments, a cloud of bur tip position tracking measurements 1104A (corresponding, for example, to measurement locations 1004, 1006) is trimmed to measurements which are at least potentially in contact with a surface of a tooth 101. Optionally, "potential contact" is evaluated, for example, by selecting position measurements which are at or near the local extremity of position measurements in the direction of the tooth surface. At block 1117, in some embodiments, selected surface tracking data is adjusted for bur tip and/or tooth geometry. In some embodiments, bur tip surface geometry is superimposed on measured position, e.g. of a centroid of the bur tip, and the union of the enclosed volume at all positions is obtained. In this case, the contact contour is optionally evaluated as the smooth surface (for some parameter of smoothness selected to represent a typical minimal size of relevant dental geometry features) which most closely approximates the extremities of the union. Optionally, this surface, and/or the surface regions which intersect with it, is used as the surface contact data 1104B which is aligned to optical scan data as now described.

Additionally or alternatively, the bur trip tracking data 1104A is converted to represent a surface by obtaining a volume comprising the union of all volumes traversed by the bur tip (and its associated volume). Then the surface of the that union which is closest to the surface of the tooth represents a complement of the tooth surface (optionally, gaps in the volume are filled in from adjoining surface data to ensure a complete surface; for example, gaps of a size below a certain threshold).

Optionally, there is an iterative procedure used to align between optically scanned oral geometry and position tracked surface geometry measurements. For example, in some embodiments, an initial approximation of a flat tooth surface (and/or a simple direction of a tooth surface) is used as just described. After fitting to an optically scanned tooth geometry 1102 (for example as described in relation to FIG. 10C and mapped contour 1002), the resulting geometry is re-evaluated for actual contact points. Such an iterative approach can be useful, for example, in the case that the tooth geometry comprises a ledge, corner, slope, or other feature which potentially interferes with the movement of the bur tip at a place away from the bur tip's leading edge.

Further reference is now made to FIG. 10C, which schematically indicates relationships between the mapped contour 1002 and a subset of position measurements 1008 taken from contour-contacting position measurements 1006. Reference is also now made to FIG. 11B, which is a flow chart schematically illustrating a method of fit-calibrating the position of a bur tip 154 in relation to an optical scan of oral geometry 1102, according to some exemplary embodiments of the present disclosure. Optionally, mapped contour 1002 corresponds to optical scan 1102, while position measurements 1008 optionally correspond to bur tip tracking data 1104.

At block 1113, in some embodiments, calibration of the relative position of position measurements 1008 to mapped contour 1002 comprises finding an optimally fitted position; for example, optimized such that the variance of a geometric transform 1010 of each point of set 1008 to mapped contour 1002 is minimized. Optionally, the transform is a linear transform. Optionally, the transform is modified by terms which allow some non-linearities, for example, to account for magnetic field distortions affecting contact position measurements. The result of the transform comprises registered bur tip tracking data 1114. Additionally or alternatively, a "space carving" approach is used, minimizing disagreement between the resultant volume re-projections.

Additional reference is now made to FIG. 10D, which schematically indicates relationships between the superset of contacting position measurements 1006 and the subset of position measurements 1008 used in alignment. Optionally, position measurements in set 1006 which do not correspond to positions of geometry known through mapped contour 1002 are found by application of a transform function 1012, which optionally comprises transform 1010, appropriately extrapolated beyond the boundaries established by the correspondence of points 1008 to mapped contour 1002.

Reference is now made to FIG. 11A, which is a flow chart schematically illustrating a method of optically calibrating the position of a bur tip 154 in relation to an optical scan of oral geometry 1102, according to some exemplary embodiments of the present disclosure.

At block 1107, in some embodiments the flowchart begins. At this block, there is received (for example, by suitably configured processing hardware) an optical scan 1102 of a portion of the oral geometry (and/or a model of oral geometry, which is optionally based on an optical scan). There is also received a bur optical scan 1106 (optionally, other optical information such as a digital photographic image) which images a portion of a dental bur 134 and/or bur tip 154 in situ together with a part of the oral geometry characterized by optical scan 1102. The received data are registered to each other, by means of which the spatial relationship of the imaged bur tip 154 (for example) to the oral geometry is determined.

At block 1109, in some embodiments, bur tip tracking data 1104, including at least one position measurement taken contemporaneously with scan 1106 is registered to the optical scan positions. Optionally, precision of registration is assisted by using a plurality of optically and magnetically tracked position calibration pairs, to produce aligned tracking data 1110, which is aligned to the in situ positions of the bur tip (that is, aligned relative to the oral geometry).

At block 1111, in some embodiments further position measurements from bur tip tracking data 1104 (those without corresponding optical scan position data) are aligned to the frame of reference of the oral geometry based on the registration from the calibration pairs which produced aligned tracking data 1110. The result is registered bur tip tracking data 1114.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of position-sensing in relation to a geometry of an oral surface for a position-sensing system, said position-sensing system comprising a probe including a probe volume, said method comprising:

receiving a 3-D model of the oral surface;

tracking positions of said probe volume by sensing a position of at least one region of said probe via a position sensor;

registering said tracked positions to said 3-D model of said oral surface based on:

a mapping between a surface at which encounters of the probe with the oral surface limit motion of said probe as tracked by said position sensor; and said 3-D model of the oral surface;

wherein:

said position sensor is an electromagnetic field sensor and is fixed onto at least one tooth, said probe comprises a rotating dental tool portion that is adapted to contact at least one of a bone surface and tooth surface for preparation thereof, said at least one region is configured to rotate with the rotation of said rotating dental tool portion, and said at least one region comprises a magnet configured such that rotation of said rotating dental tool portion rotates said magnet to thereby generate a modulated electromagnetic field sensed by said electromagnetic field sensor.

2. The method according to claim 1, wherein said probe is an elongated element extending from a distal region of a dental device.

3. The method according to claim 2, wherein said probe comprises a dental drill bur.

4. The method according to claim 3, further comprising generating an estimated tooth contour by converting a bur tip position data of a bur tip of said probe into estimated tooth contour contact regions.

5. The method according to claim 2, wherein said dental device comprises at least one camera.

6. The method according to claim 5, wherein said 3D model is generated using images acquired using said at least one camera.

7. The method according to claim 1, wherein said 3D model is generated using images acquired using an independent device comprising at least one camera.

8. The method according to claim 1, wherein said 3D model is generated and/or updated while said sensing said position of said at least one region of said probe via a position sensor.

9. The method according to claim 1, wherein said 3D model is generated off-line based on recorded positions.

10. The method according to claim 1, wherein said registering comprises determining a transform between said tracked positions and said 3-D model of the oral surface.

11. The method according to claim 10, wherein said determining comprises determining a transform with a minimized variance between sensed position measurements and said 3-D model.

12. The method according to claim 1, further comprising registering tracked positions away from the modeled oral surface, based on the transform.

13. The method according to claim 1, wherein said registering is used for calibrating an output of said position-sensing system.

14. The method according to claim 1, wherein said sensor is configured to sense a magnet mounted on said probe.

15. The method according to claim 1, wherein said sensor is configured to be fixed onto a body of said probe.

16. The method according to claim 1, wherein said tracking comprises acquiring an image including at least a portion of said oral surface and at least a portion of said probe.

17. The method according to claim 1, wherein said mapping between a surface at which encounters of the probe with the oral surface limit motion of said probe is generated by collecting a plurality of position measurement points where said encounters occur.

18. The method according to claim 17, wherein some of said plurality of position measurement points are located below a gum line.

19. The method according to claim 1, wherein said registering comprises trimming sensed position measurements, provided by said position sensor, which are at least potentially in contact with a surface of a tooth.

* * * * *